US006444824B1

(12) United States Patent
D'Ambra et al.

(10) Patent No.: US 6,444,824 B1
(45) Date of Patent: *Sep. 3, 2002

(54) PROCESS FOR PRODUCTION OF PIPERIDINE DERIVATIVES

(75) Inventors: Thomas E. D'Ambra, Wynantskill; Garry M. Pilling, East Nassau, both of NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/634,983

(22) Filed: Aug. 9, 2000

Related U.S. Application Data

(62) Division of application No. 08/576,068, filed on Dec. 21, 1995, now Pat. No. 6,153,754.

(51) Int. Cl.[7] ............................................. C07D 211/34
(52) U.S. Cl. ................. 546/210; 546/209; 546/216; 546/239; 546/240; 544/34; 544/96; 544/299; 540/469; 540/470; 540/488; 540/492
(58) Field of Search ................. 546/209, 210, 546/216, 239, 240; 544/34, 96, 299; 540/467, 470, 488, 492

(56) References Cited

U.S. PATENT DOCUMENTS

| | | | |
|---|---|---|---|
| 2,919,274 A | 12/1959 | Faust et al. .............. | 648/346.1 |
| 3,687,956 A | 8/1972 | Zivkovic .................... | 546/240 |
| 3,806,526 A | 4/1974 | Carr et al. .................. | 546/190 |
| 3,829,433 A | 8/1974 | Carr et al. .................. | 546/232 |
| 3,839,431 A | 10/1974 | Sheehan et al. ............ | 562/460 |
| 3,862,173 A | 1/1975 | Carr et al. .................. | 546/213 |
| 3,878,217 A | 4/1975 | Carr et al. .................. | 546/191 |
| 3,898,271 A | 8/1975 | Sheehan et al. ............. | 560/57 |
| 3,922,276 A | 11/1975 | Duncan et al. ............. | 546/226 |
| 3,931,197 A | 1/1976 | Carr et al. .................. | 546/237 |
| 3,941,795 A | 3/1976 | Carr et al. .................. | 546/240 |
| 3,946,022 A | 3/1976 | Carr et al. .................. | 546/191 |
| 3,956,296 A | 5/1976 | Duncan et al. ............. | 544/130 |
| 3,965,257 A | 6/1976 | Carr et al. .................. | 424/45 |
| 4,028,404 A | 6/1977 | Bays et al. ................. | 514/570 |
| 4,254,129 A | 3/1981 | Carr et al. .................. | 514/317 |
| 4,254,130 A | 3/1981 | Carr et al. .................. | 514/317 |
| 4,285,957 A | 8/1981 | Carr et al. .................. | 514/317 |
| 4,285,958 A | 8/1981 | Carr et al. .................. | 514/317 |
| 4,407,823 A | 10/1983 | Kirsch et al. .............. | 514/569 |
| 4,550,116 A | 10/1985 | Soto et al. .................. | 514/317 |
| 4,742,175 A | 5/1988 | Fawcett et al. ............. | 546/241 |
| 5,204,249 A | 4/1993 | Schwartz et al. ........... | 435/122 |
| 5,375,693 A | 12/1994 | Woosley et al. ............ | 514/317 |
| 5,578,610 A | 11/1996 | D'Ambra .................... | 514/317 |
| 5,581,011 A | 12/1996 | D'Ambra .................... | 560/8 |

FOREIGN PATENT DOCUMENTS

| | | |
|---|---|---|
| EP | 134124 | 3/1985 |
| WO | WO 93/21156 | 10/1993 |
| WO | WO 94/03170 | 2/1994 |
| WO | WO 95/00480 | 1/1995 |
| WO | WO 95/00482 | 1/1995 |

OTHER PUBLICATIONS

Meyers et al., "Oxazolines. IX. Synthesis of Homologated Acetic Acids and Esters," *J. Org. Chem.*, 39:2778–2783 (1974).

Meyers et al., "Oxazolines. X. Synthesis of γ–Butyrolactones," *J. Org. Chem.*, 39:2783–2787 (1974).

Meyers et al., "Oxazolines. XI. Synthesis of Functionalized Aromatic and Aliphatic Acids. A Useful Protecting Group for Carboxylic Acids against Grignard and Hydride Reagents," *J. Org. Chem.*, 39:2787–2793 (1974).

Milstein et al., "A General, Selective, and Facile Methods for Ketone Synthesis from Acid Chlorides and Organotin Compounds Catalyzed by Palladium," *Journal of the American Chemical Society*, 100:3636–3638 (1978).

(List continued on next page.)

*Primary Examiner*—Celia Chang
(74) *Attorney, Agent, or Firm*—Nixon Peabody LLP

(57) ABSTRACT

The present invention relates to a method for preparing piperidine derivative compounds by converting, with a piperidine compound, regioisomers having the formula:

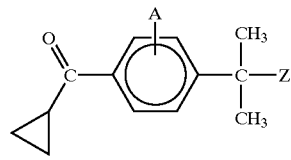

where Z is

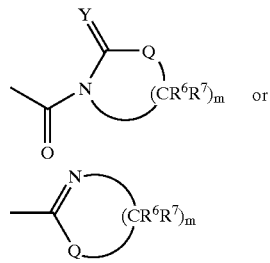

and where m is 1 or 3–6; Q and Y are the same or different and are selected from the group consisting of O, S, and $NR^5$; $R^6$ and $R^7$ are the same or different and are selected from the group consisting of hydrogen, an alkyl moiety, an aryl moiety, $OR^8$, $SR^8$, and $NR^8R^9$; and $R^5$, $R^8$, and $R^9$ are the same or different and are selected from the group consisting of hyrogen, an alkyl moiety, and an aryl moiety.

42 Claims, No Drawings

OTHER PUBLICATIONS

Milstein et al., "Mild, Selective, General Method of Ketone Synthesis from Acid Chlorides and Organotin Compounds Catalyzed by Palladium," *J. Org. Chem.*, 44:1613–1618 (1979).

March, *Advanced Organic Chemistry: Reactions, Mechanisms, and Structure*, 4th Ed., New York: John Wiley & Sons, pp. 478–479 and 661–662 (1992).

Buehler et al., "Organic Syntheses," *Wiley Interscience* p. 789 (1970).

Fishwick et al., "An Efficient Route to S–N–(9–Fluorenylmethoxycarbonyl)–4'–(1–azi–2,2,2–trifjuoroethyl)phenylalanine," *Tetrahedron Letters*, 35:4611–4614 (1994).

Neubold, "Cyclic Imido Acid Esters," Ca 79:92196 (1973).

Boell et al., "2–Pyridinols," CA 90:6252 (1978).

Caujolle et al., "Synthesis Antiparasitic and Antifungal Activities of Arylakyl and Arylvinylthiazolines," CA 119:139162 (1993).

Clarke et al., "A Facile One Stage Synthesis of Oxazolines Under Microwave Irradiation," CA 124:317042 (1996).

Meyers et al., "Synthesis via Oxazolines. A Highly Stereoselective Synthesis of (+/–)–cis–2–Methyl Cyclopentanecarboxylic Acid, Via a Kinetically Controlled Cyclization," *J.C.S. Chem. Comm.* pp. 768–770 (1974).

Swain et al., "Novel–HT3 Antagonists: Indol–3–yllspiro(azabicycloalkane–3,5'(4"H)oxazoles)," *J. Med. Chem.* 35(6):1019–31 (1992).

Kawai et al., "A Facile Synthesis of an Oxidation Product of Terfenadine," *J. Org. Chem.* 59:2620–22 (1994).

Murugesan et al., "Prepareation of N–isoxazolylbiphenylsulfonamides as Endothelin Antagonists," CA 125:10795 (1996).

Busacca et al., "A One Step Synthesis of Thiazolines from Esters," CA 125:58380 (1996).

K.Y. Chan, et al., "Direct enantiomeric separation of terfenadine and its major acid metabolite by high–performance liquid chromatography, and the lack of stereoselective terfenadine enantiomer biotransformation in man," *Journal of Chromatography*, 271:291–97 (1991).

F.J. McCarty, et al., "Central Depressants. Phosphoramidates Derived from α,α–Disubstituted 4–Piperidinemethanols," *Department of Organic Research, Scientific Laboratories*, (1961).

Chemical Abstract, vol. 94, 1981, pp. 644, 94:15678e.

Chemical Abstract, vol. 110, 1989, pp. 762, 110:173097e.

Woosley, R.L., et al. "Mechanism of the Cardiotoxic Actions of Terfenadine," *JAMA* 269 (12):1532–36 (Mar. 1993).

Honig, P.K., et al. "Terfenadine–ketoconazole Interaction. Pharmacokinetic and Electrocardiographic Consequences," *JAMA*, 269 (12):1513–18 (Mar. 1993).

Kuhlman, J.J., Jr., "Measurement of Azacyclonol in Urine and Serum of Humans Following Terfenadine (Seldane) Administration Using Gas Chromatography–mass Spectrometry," *J. Chromatogr.* 578 (2):207–13 (Jul. 1992).

Honig, P.K., et al., "Changes in the Pharmacokinetics and Electrocardiographic Pharmacodynamics of Terfenadine with Concomitant Administration of Erythromycin," *Clin. Pharmacol. Ther.* 52(3): 231–8 (Sep. 1992).

Chen, T.M., et al., "Determination of the Metabolites of Terfenadine in Human Urine by Thermospray Liquid Chromatography–Mass Spectrometry," *J. Pharm. Biomed. Anal.* 9(10–12):929–33, (1991).

Eller et al., "Pharmacokinetics of Terfenadine in Healthy Elderly Subjects," *J. Clin. Pharmacol.* 32(3):267–71 (1992).

Coutant et al., "Determination of Terfenadine and Terfenadine Acid Metabolite in Plasma Using Solid–Phase Extraction and High–Performance Liquid Chromatography with Fluorescence Detection," *J. Chromatogr.* 570(1):139–48 (1991).

Luo, H., et al. "N(+)–glucuronidation of Aliphatic Tertiary Mines, A General Phenomenon in the Metabolism of H1–antihistamines in Humans," *Xenobiotca.*, 21(10):1281–8 (Oct. 1991).

Estelle, F., et al., "Pharmacokinetic Optimisation of Histamine H1–Receptor Antagonist Therapy," *Clin. Pharmacokinet.*, 21(5):372–93 (Nov. 1991).

Shall, L. et al., "Dose–Response Relationship Between Objective Measures of Histamine–Induced Weals and Dose of Terfenadine," *Acta. Derm. Venereol.* 71(3):199–204 (1991).

Campoli–Richards, D.M., et al., "Cetirizine. A Review of its Pharmacological Properties and Clinical Potential in Allergic Rhinitis, Pollen–Induced Asthma, and Chronic Urticaria," *Drugs* 40(5)762–81 (Nov. 1990).

Snowman, A.M., et al., "Cetirizine: Actions on Neurotransmitter Receptors," *J. Allergy Clin. Immunol.* 86(6–2)1025–8 (Dec. 1990).

Berman, B.D., "Perennial Allergic Rhinitis: Clinical Efficacy of a New Antihistamine," *J. Allergy Clin. Immunol.* 86 (68–2)1004– (Dec. 1990).

Monahan, B.P., et al., "Torsades de Pointes Occurring in Association with Terfenadine Use," *JAMA*, 264(21) 2788–90 (Dec. 1990).

Simons, K.J., et al., "Pharmacokinetics and Pharmacodynamics of Terfenadine and Chlorpheniramine In the Elderly," *J. Allergy Clin. Immunol.* 85(3)540–7 (Mar. 1990).

Sweeney, G.D., et al., "Anti–Allergy and Anti–Asthma Drugs. Disposition in Infancy and Childhood," *Clin. Pharmacokinet*, 17 Suppl (1):156–68 (1989).

Coniglio, A.A., "Effect of Acute and Chronic Terfenadine on Free and Total Serum Phenytoin Concentrations in Epileptic Patients," *Epilepsia* 30(5):611–6 (Sep.–Oct. 1989).

Mann, K.V., et al., "Nonsedating Histamine H1–Receptor Antagonists," *Clin. Pharm.* 8(5):331–44 (May 1898).

Barenhotz, H.A., "Loratadine: A Non Sedating Antihistamine with Once–Daily Dosing," *DICP* 23(6)44550 (Jun. 1989).

Brion et al., "Lack of Effect of Terfenadine on Theophylline Pharmacokinetics and Metabolism in Normal Subjects." *Br. J. Clin. Pharmacol.*, 27(3)391–5 (1989).

Kaliner "Non–sedating Antihistamines," *Allergy Proc.* 9(6):649–63 (1988).

Maurer, H., et al., "Identification and Differentiation of Alkylamine Antihistamines and Their Metabolites I Urine by Computerized Gas Chromatography–Mass Spectrometry," *J. Chromatogr.* 430(1):31–31 (Aug. 1988).

Simons, F.E., et al., "Lack of Subsensitivity to Terfenadine During Long–Term Terfenadine Treatment," *J. Allergy Clin. Immunol.* 82(6):1068–75 (Dec. 1988).

Shall, L., et al., "Assessment of the Duration of Action of Terfenadine on Histamine Induced Weals," *Br. J. Dermatol.* 119(4):525–31 (Oct. 1988).

Akagi, M., "Antiallergic Effects of Terfenadine on Immediate Type Hypersensitivity Reactions," *Immunopharmacol. Immunotoxicol.* 9(2–3):257–79 (1987).

Snyder, S.H., et al., "Receptor Effects of Cetirizine," *Ann. Allergy* 59(6–2):4–8 (Dec. 1987).

Simons, F.E., "The Pharmacokinetics and Pharmacodynamics of Terfenadine in Children," *J. Allergy Clin. Immunol.* (6):884–90 (1987).

Carter, C.A., et al., "Terfenadine, A Nonsedating Antihistamine," *Drug Intell. Clin. Pharm.* 19(11):812–7 (Nov. 1985).

Paton, D.M., et al., Clinical Pharmacokinetics of H1–Receptor Antagonists (He Antihistamines) *Clin. Pharmacokinet*, 10(6):477–97 (Nov.–Dec. 1985).

Woodward, J.K., "Terfenadine, the First Non–Sedating Antihistamine," *Arzneimittelforschung* 32(9a):1154–6 (1982).

Cook, C.E., et al., "Radioimmunoassay for Terfenadine in Human Plasma," *J. Pharm. Sci.* 69(12):1419–23 (Dec. 1980).

Sepracor Inc. Announces Second Quarter 1993 Financial Results, *Business Wire, Inc.* (Jul. 1993).

Marion Merrell Dow Restructures, *The Financial Times Limited* (Jul. 1993).

Marion Merrell Invests in Sepracor, *Chemical Week Associates* (Jun. 1993).

Sepracor, Inc. Announces Agreement with Marion, *Business Wire, Inc.* (Jun. 1993).

Sepracor Licenses Rights to Marion Merrell, *Reuters, Limited* (Jun. 1993).

Drug Makers Contend with Inevitable Change, *Chemical Week Associates* (Mar. 1993).

Drug Pipelines Point to a Mixed Future, *Chemical Week Associates* (Mar. 1993).

Not Associated with Cardiac Effects of Leading Prescription, Non–sedative Antihistamines; JAMA Study First to Demonstrate Potential Therapeutic Benefits of Active Metabolite of Terfenadine, *Business Wire, Inc.* (Mar. 1993).

R.T. Morrison, et al., *Organic Chemistry*, pp. 661–662 (3rd ed., 1974).

Moragues, et al., "Ebastine," *Drugs of the Future* 15(7):674–679 (1990).

Mattila, et al., "Lack of Pharmacodynamic and Pharmacokinetic Interactions of the Antihistamine Ebastine With Ethanol in Healthy Subjects," *Eur. J. Clin. Pharmacol.* 43:179–184 (1992).

Zamani et al., "Enantiomeric Analysis of Terfenadine in Rat Plasma by HPLC," *Chirality* 3(6)467–70 (1991).

Eller et al., Absence of Food Effects on the Pharmacokinetics of Terfenadine,: Biopharm. Drug Dispos. 13(3):171–7 (1992).

Chan et al., Direct Enantiomeric Separation of Terfenadine and its Major Acid Metabolite by High–Performance Liquid Chromatography, and the Lack of Stereoselective Terfenadine Enantiomer Biotransformation in Man,: *J. Chromatogr.* 571:291–7 (1991).

Greene et al., "Protective Groups in Organic Synthesis," John Wiley & Sons, publishers, p. 224–226, 265, 270–271 (1991).

PROCESS FOR PRODUCTION OF PIPERIDINE DERIVATIVES

This application is a divisional of U.S. patent application Ser. No. 08/576,068, filed Dec. 21, 1995, now U.S. Pat. No. 6,153,754, which is hereby incorporated by reference.

FIELD OF THE INVENTION

The present invention relates to processes for the production of piperidine derivatives.

BACKGROUND OF THE INVENTION

Terfenadine, 1-(p-tert-butylphenyl)-4- [4'-(α-hydroxydiphenylmethyl)-1'-piperidinyl]-butanol is a non-sedating anti-histarnine. It is reported to be a specific $H^1$-receptor antagonist that is also devoid of any anticholingeric, anti-serotoninergic, and anti-adrenergic effects both in vitro and in vivo. See D. McTavish, K. L. Goa, M. Ferrill, Drugs, 1990, 39, 552; C. R. Kingsolving, N. L. Monroe, A. A. Carr, *Pharmacologist*, 1973, 15, 221; J. K. Woodward, N. L. Munro, *Arzneim-Forsch*, 1982, 32, 1154; K. V. Mann, K. J. Tietze, *Clin. Pharm.* 1989, 6, 331. A great deal of effort has been made investigating structure-activity relationships of terfenadine analogs, and this is reflected in the large number of U.S. patents disclosing this compound and related structures as follows:

U.S. Pat. No. 3,687,956 to Zivkovic
U.S. Pat. No. 3,806,526 to Carr, et. al.
U.S. Pat. No. 3,829,433 to Carr, et. al.
U.S. Pat. No. 3,862,173 to Carr, et. al.
U.S. Pat. No. 3,878,217 to Carr, et. al.
U.S. Pat. No. 3,922,276 to Duncan, et. al.
U.S. Pat. No. 3,931,197 to Carr, et. al.
U.S. Pat. No. 3,941,795 to Carr, et. al.
U.S. Pat. No. 3,946,022 to Carr, et. al.
U.S. Pat. No. 3,956,296 to Duncan, et. al.
U.S. Pat. No. 3,965,257 to Carr, ct. al.
U.S. Pat. No. 4,742,175 to Fawcett, et. al.

In animal and human metabolic studies, terfenadine has been shown to undergo extensive hepatic first-pass metabolism, and after usual dosages it cannot be detected in plasma unless very sensitive assayls are used. A specific hepatic cytoclrome P-450 enzyme converts terfenadine to the major metabolite 4-[4-[4-(hydroxydiphenylmethyl)-1-piperidinyl]-1-hydrox),butyl]-α-α-dimethylphenylacetic acid, also known as terfenadine carboxylic acid metabolite. This metabolite can be readily detected in plasma and is considered to be the active form of orally administered terfenadine.

Side effects reported ws ith terfenadine are cardiac arrhythmias (ventricular tachyarrhythmias, torsades de points, ventricular fibrillation), sedation, GI distress, dry mouth, constipation and/or diarrhea. The most serious of these, and potentially life threatening, are cardiac arrhythlmias, which are related to terfenadine's ability to prolong the cardiac QT interval, and are only reported in patients administered terfenadine with liver disease or who also take the antifungal drug ketoconazole or the antibiotic erythromycin. As a result of these adverse events, the FDA, in 1992, required terfenadine to include a warning label.

Although OTC formulations of terfenadine are purportedly being developed, the potentially serious side effects seen in some patients will be a significant obstacle for regulatory approval.

Since cardiac side effects of terfenadine have been reported in patients with impaired liver function, as well as in patients also taking antibiotics known to suppress hepatic enzyme function, it was speculated that the cardiac side effects were due to accumulation of terfenadine and not due to accumulation of terfenadine carboxylic acid metabolite. Patch clamp studies in isolated feline ventricular myocytes support the contention that terfenadine, and not the carboxylic acid metabolite, is responsible for cardiac side effects. At a concentration of 1 $\mu$M, terfenadine caused a greater than 90% inhibition of the delayed rectifier potassium current. At concentrations up to 5 $\mu$M, the terfenadine carboxylic acid metabolite had no significant effect on the potassium current in this assay (See R. L. Woosley, Y. Chen, J. P. Frieman, and R. A. Gillis, *JAMA* 1993, 269, 1532). Since inhibition of ion transport has been linked to cardiac abnormalities such as arrhythmias, these results indicate that terfenadine carboxylic acid is likely not liable to cause cardiac arrhythmias, at dose levels at which there is a distinct risk of such a side effect being caused by terfenadine itself.

Carebastine, 4-[4-[4-(diphenylmethoxy)-1-piperidinyl]-1-oxobutyl]-α,α-dimethylphenylacetic acid, is the carboxylic acid metabolite of ebastine, 1-(p-tert-butylphenyl)-4-[4'-(α-diphenylmethoxy)-1'-piperidinyl]-butanol. Both compounds possess potent selective histamine $H_1$-receptor blocking and calcium antagonist properties and should prove useful in the treatment of a variety of respiratory, allergic, and cardiovascular disease states.

These compounds relax bronchial and vascular smooth muscle in vitro and in vivo and inhibit the constrictor influence of noradrenaline, potassium ions, and various other agonist drugs. The compounds also inhibit responses of intestinal and tracheal preparations to histamine, acetylcholine, and barium chloride and block the bronchoconstriction induced by histamine aerosol in guinea pigs in doses less than 1 mg/kg animal body weight administered orally. They also possess antianaphylactin properties in the rat, inhibit the skin lesions to a variety of anaphylactic mediators (histamine, 5-hydroxytryptamine, bradykinin, $LCD_4$, etc.), and antagonize the Schultz-Dalc response in the sensitive guinea-pig.

Piperidine derivatives related to the terfenadine carboxylic acid metabolite are disclosed in the following U.S. patents:

U.S. Pat. No. 4,254,129 to Carr, et. al.
U.S. Pat. No. 4,254,130 to Carr, et. al.
U.S. Pat. No. 4,285,957 to Carr, et. al.
U.S. Pat. No. 4,285,958 to Carr, et. al.

In these patents, 4-[4-[4-(hydroxydiphenylmethyl)-1-piperidinyl]-1-hydroxybutyl]-α,α-dimethylbenzeneacetic acid and related compounds are prepared by alkylation of a substituted piperidine derivative of the formula:

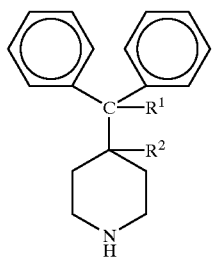

with an ω-haloalkyl substituted phenyl ketone of the formula:

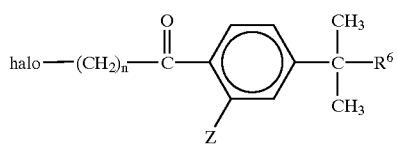

wherein the substituents halo, $R^1$, $R^2$, n, Z, and $R^6$ are described in column 6 of U.S. Pat. No. 4,254,130.

In similar fashion, U.S. Pat. No. 4,550,116 to Soto et al. describes preparation of piperidine derivatives related to carebastine by reacting the ω-haloalkyl substituted phenyl ketone with a substituted hydroxypiperidine derivative of the formula:

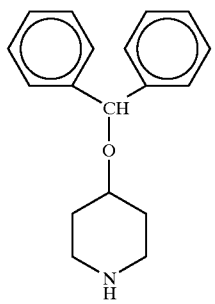

U.S. Pat. No. 4,254,130 indicates that ω-haloalkyl substituted phenyl ketones, wherein Z is hydrogen, are prepared by reacting an appropriate straight or branched lower alkyl $C_{1-6}$ ester of α-α-dimethylphenylacetic acid with a compound of the following formula:

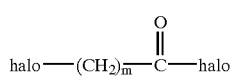

under the general conditions of a Friedel-Crafts acylation, wherein halo and m are described in column 11 of U.S. Pat. No. 4,254,129. The reaction is carried out in carbon disulfide as the preferred solvent.

Other procedures for producing terfenadine carboxylic acid metabolite are disclosed in PCT Application Nos. WO95/00482, WO94/03170, and WO95/00480.

The present invention is directed toward an improved process for preparation of terfenadine carboxylic acid metabolite and carebastine.

SUMMARY OF THE INVENTION

The present invention relates to processes for preparing piperidine derivative compounds of the formulae:

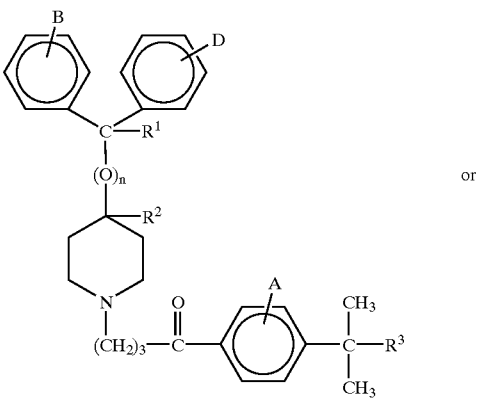

or

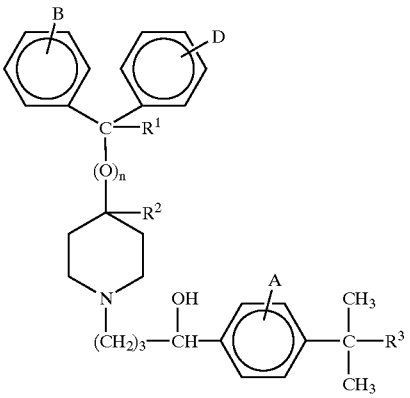

wherein n is 0 or 1;

$R^1$ is hydrogen or hydroxy;

$R^2$ is hydrogen;

or, when n is 0, $R^1$ and $R^2$ taken together form a second bond between the carbon atoms bearing $R^1$ and $R^2$, provided that when n is 1, $R^1$ and $R^2$ are each hydrogen;

$R^3$ is —COOH or —COOR$^4$;

$R^4$ is an alkyl or aryl moiety;

A, B, and D are the substituents of their rings, each of which may be different or the same, and are selected from the group consisting of hydrogen, halogens, alkyl, hydroxy, alkoxy, and other substituents or a salt thereof The piperidine derivative compound is prepared by providing a regioisomer having the following formula:

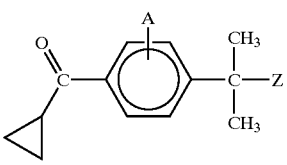

wherein

Z is —CG$^1$G$^2$G$^3$,

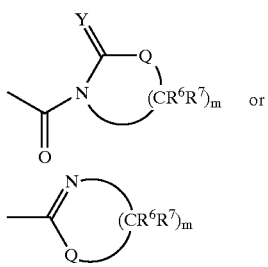 or m is an integer from 1 to 6;

Q and Y are the same or different and are selected from the group consisting of O, S, and NR$^5$;

G$^1$, G$^2$, and G$^3$ are the same or different and are selected from the group consisting of OR$^8$, SR$^8$, and NR$^8$R$^9$;

R$^6$ and R$^7$ are the same or different and are selected from the group consisting of hydrogen, an alkyl moiety, an aryl moiety, OR$^8$, SR$^8$, and NR$^8$R$^9$; and R$^5$, R$^8$, and R$^9$ are the same or different and are selected from the group consisting of hydrogen, an alkyl moiety, and an aryl moiety.

The regioisomer is then converted to the piperidine derivative having a keto group with a piperidine compound.

The invention further relates to a regioisomer having the formula:

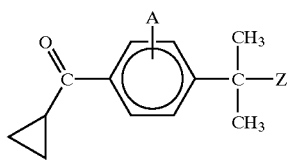

The present invention is also directed to processes for preparing a regioisomer having the formula:

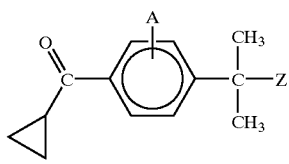

In one aspect of the invention, the process for preparing the regioisomer includes acylating an α,α-disubstituted-methylbenzene derivative having the formula:

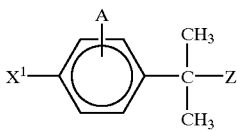

wherein

X$^1$ is a halogen, trialkyl or triaryl tin, trialkyl or triaryl borate, alkylhalo silicon, trialkyl silicon, a substituted sulfonic ester, or substituents useful in organometallic coupling reactions with a compound having the formula:

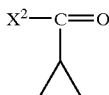

wherein

X$^2$ is a halogen; an alkali metal oxide; a moiety having the formula —OR$^{10}$; a moiety having the formula —SR$^{10}$; or an amine; and R$^{10}$ is selected from the group consisting of hydrogen, an alkyl moiety, and an aryl moiety under conditions effective to produce the regioisomer.

In another aspect of the present invention, the process for preparing the regioisomer includes reacting a 4-(α,α-disubstituted)-toluic acid derivative having the formula:

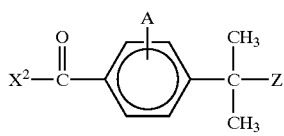

wherein

X$^2$ is hydrogen; a halogen; an alkali metal oxide; a moiety having the formula —OR$^{10}$: a moiety having the formula —SR$^{10}$; or an amine; and R$^{10}$ is selected from the group consisting of hydrogen, an alkyl moiety, and an aryl moiety with a compound having the formula:

wherein

X$^1$ is a halogen, trialkyl or triaryl tin, trialkyl or triaryl borate, alkylhalo silicon, trialkyl silicon, a substituted sulfonic ester, or substituents useful in organometallic coupling reactions under conditions effective to produce the regioisomer.

In yet another aspect of the invention, the process of preparing a regioisomer includes providing an α,α-diunsubstituted regioisomer precursor having the formula:

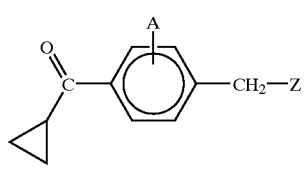

and methylating the α,α-diunsubstituted regioisomer precursor under conditions effective to produce the regioisomer.

The present invention is also directed to an α,α-disubstituted-methylbenzene derivative having the formula:

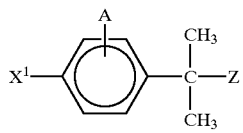

and to an α,α-diunsubstituted-methylbenzene derivative having the formula:

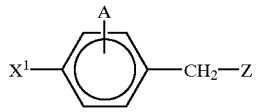

The invention further relates to an oxobutyl derivative having the formula:

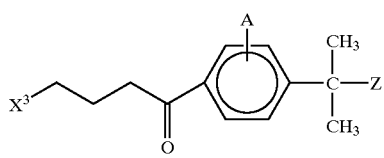

as well as to piperidine derivative precursors having the formulae:

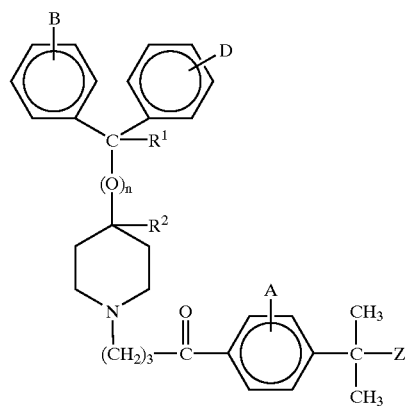

or

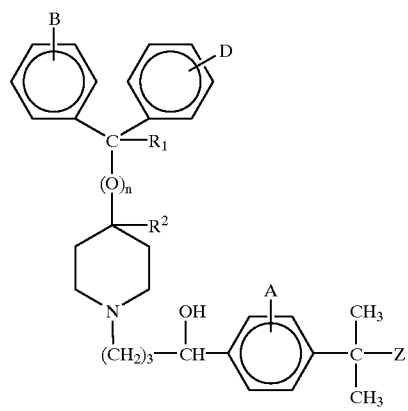

DETAILED DESCRIPTION OF THE INVENTION

The present invention relates to a process for preparing piperidine derivative compounds having the formulae:

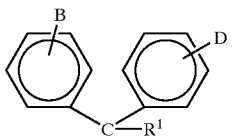

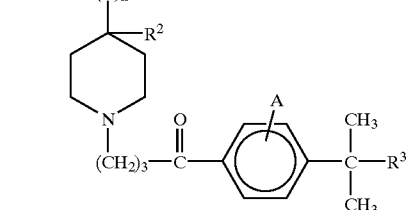

or

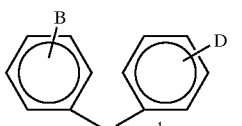

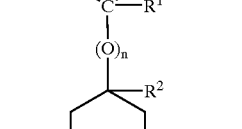

wherein
n is 0 or 1;
$R^1$ is hydrogen or hydroxy;
$R^2$ is hydrogen; or, when n is 0, $R^1$ and $R^2$ taken together form a second bond between the carbon atoms bearing $R^1$ and $R^2$, provided that when n is 1, $R^1$ and $R^2$ are each hydrogen;
$R^3$ is —COOH or —COOR$^4$;
$R^4$ is an alkyl or aryl moiety;
A, B, and D are the substituents of their rings, each of which may be different or the same, and are selected from the group consisting of hydrogen, halogens, alkyl, hydroxy, alkoxy, and other substituents
or a salt thereof.

These piperidine derivative compounds may be in the form of 4-diphenylmethylpiperidine derivatives represented by the following formulae:

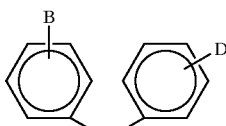

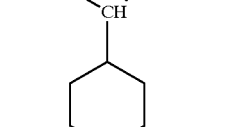

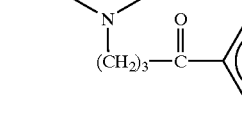

-continued or

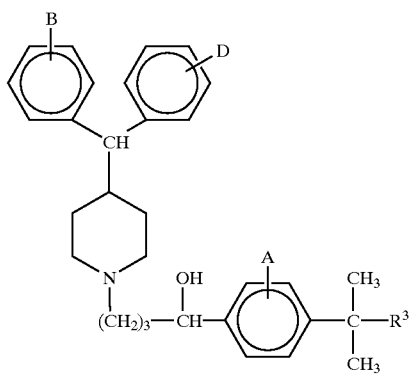

where A, B, D, and $R^3$ are defined above. The piperidine derivative compounds also include 4-(hydroxydiphenylmethyl)piperidine derivatives according to the following formulae:

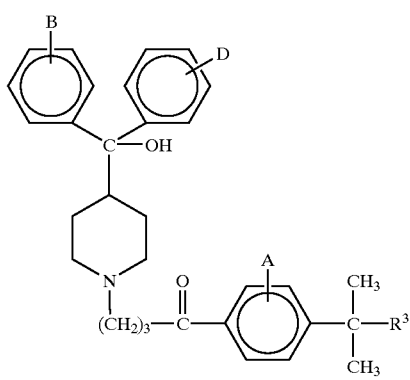

or

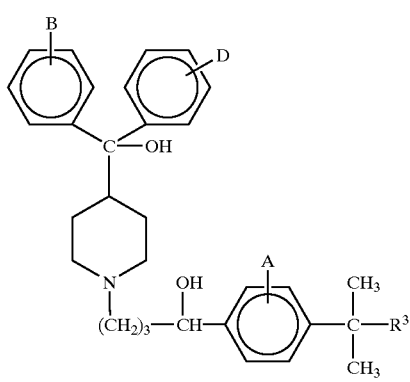

where A, B, D, and $R^3$ are defined above. Another useful class of piperidine derivative compounds are 4-diphenylmethylenepiperidine derivatives in accordance with the following formulae:

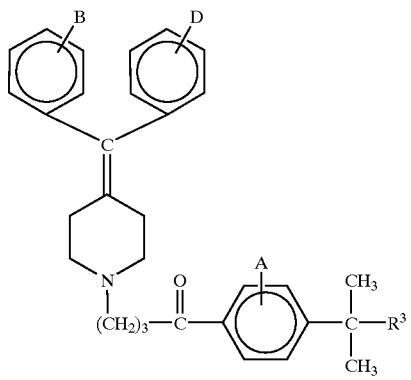

or where A, B, D, and $R^3$ are defined above.

Another useful class of piperidine derivative compounds are 4-diphenylmethoxypiperidine derivatives having the following fonnulac:

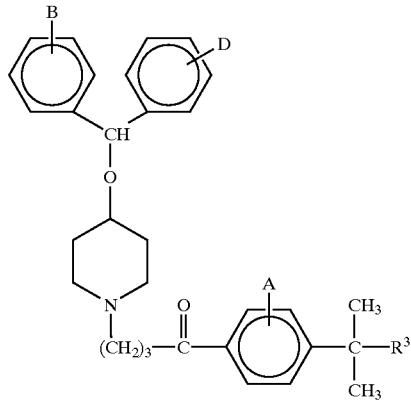

or

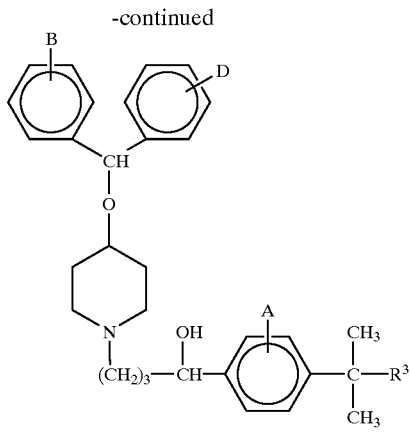

where A, B, D, and R³ are defined above.

Examples of R⁴ are substituted or unsubstituted, straight or branched alkyl groups, including methyl, ethyl, n-propyl, isopropyl, n-butyl, sec-butyl, tert-butyl, n-pentyl, neopentyl, n-hexyl, benzyl, and 4-methylbenzyl groups and substituted or unsubstituted aryl groups, including phenyl, tolyl, and xylyl groups.

Illustrative examples of compounds prepared by the process of the present invention are as follows:

4-[4-[4-(hydroxydiphenylmethyl)-1-piperidinyl]-1-hydroxybutyl]-α,α-dimethylbenzeneacetic acid;

4-[4-[4-(diphenylmethyl)-1-piperidinyl]-1-hydroxybutyl]-α,α-dimethylbenzeneacetic acid;

4-[4-[4-(diphenylmethylene)-1-piperidinyl]-1-hydroxybutyl]-α,α-dimethylbenzeneacetic acid;

4-[4-[4-(hydroxydiphenylmethyl)-1-piperidinyl]-1-hydroxybutyl]-α,α-dimethyl-3-hydroxybenzeneacetic acid;

4-[4-[4-hydroxydiphenylmethyl)-1-piperidinyl]-1-hydroxybutyl]-α,α-dimethyl-2-hydroxybenzeneacetic acid;

4-[4-[4-(diphenylmethylene)-1-piperidinyl]-1-hydroxybutyl]-α,α-dimethyl-3-hydroxybenzeneacetic acid;

4-[4-[4-(diphenylmethylene)-1-piperidinyl]-1-hydroxybutyl]-α,α-dimethylbenzeneacetic acid;

ethyl 4-[4-[4-(hydroxydiphenylmethyl)-1-piperidinyl]-1-hydroxybutyl]-α,α-dimethylbenzeneacetate;

n-pentyl 4-[4-[4-(diphenylmethyl)-1-piperidinyl]-1-hydroxybutyl]-α,α-dimethylbenzeneacetate;

ethyl 4-[4-[4-(diphenylmethylene)-1-piperidinyl]-1-hydroxybutyl]-α,α-dimethylbenzeneacetate;

methyl 4-[4-[4-(hydroxydiphenylmethyl)-1-piperidinyl]-1-hydroxybutyl]-α,α-dimethylbenzeneacetate;

ethyl 4-[4-[4-(hydroxydiphenylmethyl)-1-piperidinyl]-1-hydroxybutyl]-α,α-dimethyl-(3-hydroxybernzene)acetate;

n-propyl 4-[4-[4-(hydroxydiphenylmethyl)-1-piperidinyl]-1-hydroxybutyl]-α,α-dimethyl-(2-hydroxybenzene)acetate;

n-hexyl 4-[4-[4-(diphenylmethylene)-1-piperidinyl]-1-hydroxybutyl]-α,α-dimethyl-(3-hydroxybenzene)acetate;

ethyl 4-[4-[4-(diphenylmethylene)-1-piperidinyl]-1-hydroxybutyl]-α,α-dimethylbenzeneacetate;

4-[4-[4-(diphenylmethoxy)-1-piperidinyl]-1-hydroxybutyl]-α,α-dimethylbenzeneacetic acid;

4-[4-[4-(diphenylmethoxy)-1-piperidinyl]-1-hydroxybutyl]-α,α-dimethyl-3-hydroxybenzeneacetic acid;

4-[4-[4-(diphenylmethoxy)-1-piperidinyl]-1-hydroxybutyl]-α,α-dimethyl-2-hydroxybenzeneacetic acid;

4-[4-[4-(diphenylmethoxy)-1-piperidinyl]-1-hydroxybutyl]-α,α-dimethyl-3-hydroxybenzeneacetic acid;

4-[4-[4-(diphenylmethoxy)-1-piperidinyl]-1-hydroxybutyl]-α,α-dimethylbenzeneacetic acid;

n-pentyl 4-[4-[4-(diphenylmethoxy)-1-piperidinyl]-1-hydroxybutyl]-α,α-dimethylbenzeneacetate;

ethyl 4-[4-[4-(diphenylmethoxy)-1-piperidinyl]-1-hydroxybutyl]-α,α-dimethylbenzeneacetate;

ethyl 4-[4-[4-(diphenylmethoxy)-1-piperidinyl]-1-hydroxybutyl]-α,α-dimethyl-(3-hydroxybenzene)acetate;

n-propyl 4-[4-[4-(diphenylmethoxy)-1-piperidinyl]-1-hydroxybutyl]-α,α-dimethyl-(2-hydroxybenzene)acetate;

n-hexyl 4-[4-[4-(diphenylmethoxy)-1-piperidiiyl]-1-hydroxybutyl]-α,α-dimethyl-(3-hydroxybenzene)acetate; and ethyl 4-[4-[4-(diphenylmethoxy)-1-piperidinyl]-1-hydroxybutyl]-α,α-dimethylbenzeneacetate.

Particularly preferred are compounds of the formulae:

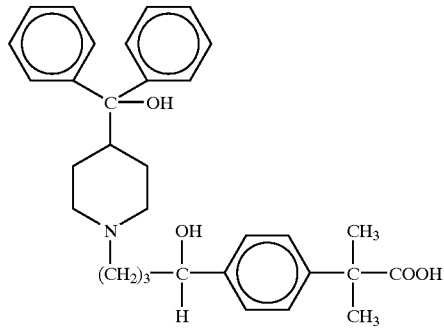

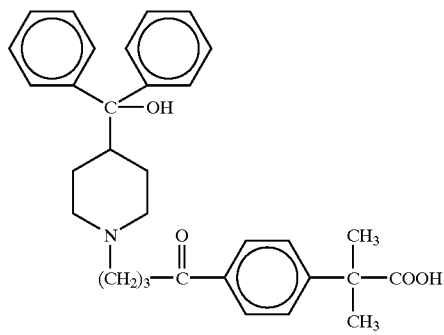

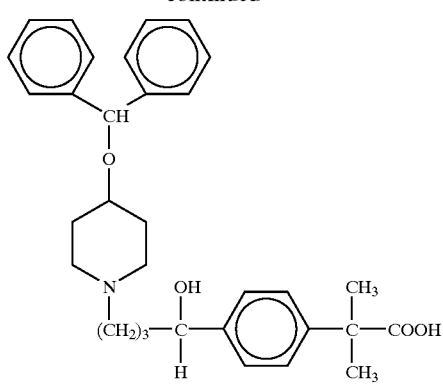

and

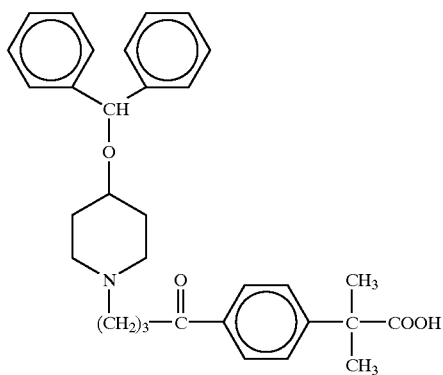

Optionally, both phenyl groups from the piperidine compound may be alkyl (e.g., methyl, substituted at the position para to the methylene, such as

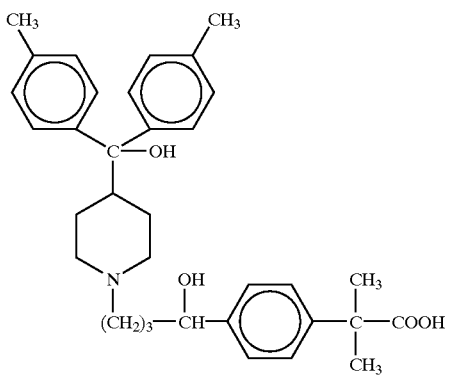

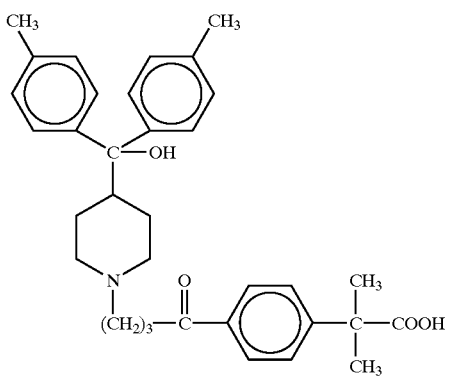

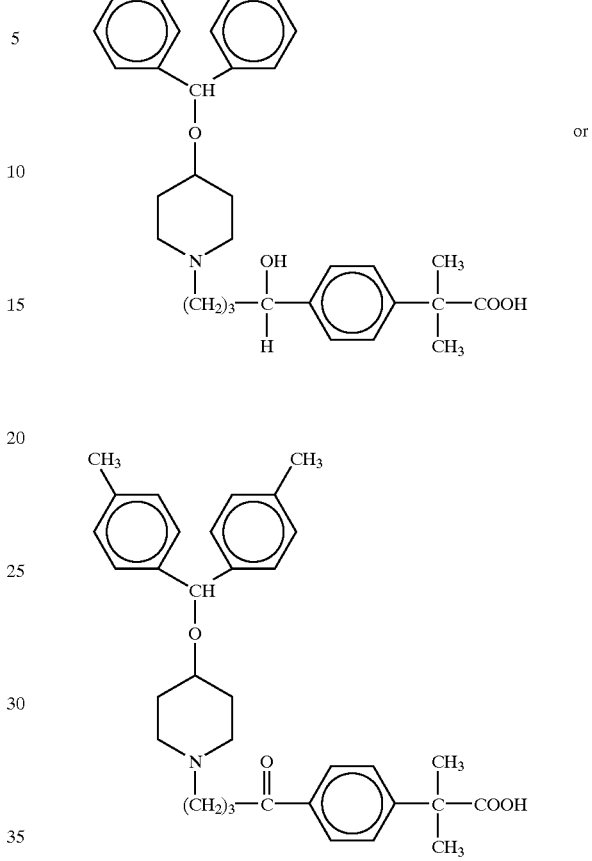

or

The compounds prepared by the methods of the present invention can be pharmaceutically acceptable salts in the form of inorganic or organic acid or base addition salts of the above compounds. Suitable inorganic acids are, for example, hydrochloric. hydrobromic, sulfuric, and phosphoric acids. Suitable orcanic acids include carboxylic acids, such as, acetic, propionic, glycolic, lactic, pyruvic. malonic, succinic, fumanec, malic, tartaric, citric, cyclamic, ascorbic, maleic, hydroxymaleic, dihydroxymaleic, benzoic, phenylacetic, 4-aminobenzoic, anthranilic, cianamic, salicylic, 4-aminosalicylic, 2-phenoxybenzoic, 2-acetoxybenzoic, and mandelic acid. Sulfonic acids, such as, methanesulfonic, ethanesulfonic, and β-hydroxyethanesulfonic acid are also suitable acids. Non-toxic salts of the compounds of the above-identified formulae formed with inorganic and organic bases include, for example, those alkali metals, such as, sodium, potassium, and lithium, alkaline earth metals, for example, calcium and magnesium, light metals of group IIIA, for example, aluminum, organic amines, such as, primary, secondary, or tertiary amines, for example, cyclohexylamine, ethylamine, pyridine, methylaminoethanol, and piperazine. These salts are prepared by conventional means, for example, by treating the piperidime derivative compounds of the formulae:

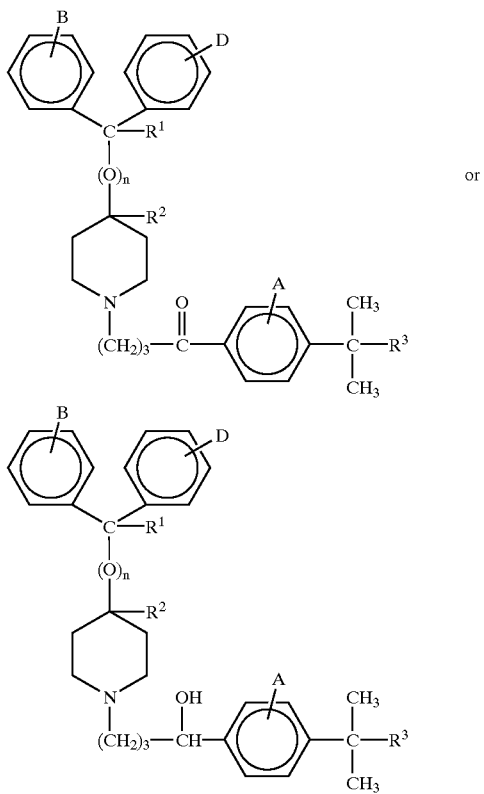

where A, B, D, n, $R^1$, $R^2$, and $R^3$ are defined above, with an appropriate acid or base.

The piperidine derivative compounds prepared by the methods of the present invention can be utilized as the biologically active components in pharmaceutical compositions. These compounds are useful as antihistamines, antiallergy agents, and bronchodilators. They may be administered alone or with suitable pharmaceutical carriers, and can be in solid or liquid form such as, tablets, capsules, powders, solutions, suspensions, or emulsions.

The compounds prepared by the methods of this invention can be administered orally, parenterally, for example, subcutaneously, intravenously, intramuscularly, intraperitoneally, by intranasal instillation or by application to mucous membranes, such as, that of the nose, throat, and bronchial tubes. Such application to mucous membranes can be achieved with an aerosol spray containing small particles of a compound of this invention in a spray or dry powder form.

The quantity of the compound administered will vary depending on the patient and the mode of administration and can be any effective amount. The quantity of the compound administered may vary over a Aide range to provide in a unit dosage an effective amount of from about 0.01 to 20 mg/kg of body weight of the patient per day to achieve the desired effect. For example, the desired antihistamine, antiallergy, and bronchodilator effects can be obtained by consumption of a unit dosage form such as a tablet containing 1 to 50 mg of the compound of the present invention taken 1 to 4 times daily.

The solid unit dosage forms can be of the conventional type. This solid form can be a capsule, such as an ordinary gelatin type containing the compound of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The compounds prepared according to this invention may also be administered in injectable dosages by solution or suspension of the compounds of the present invention in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the compounds in solution or suspension may be packaged in a pressurized aerosol container together with suitable propellants, for example, hydrocarbon propellants like propane, butane. or isobutane with conventional adjuvants. These compounds may be administered in a non-pressurized foirn, such as in a nebulizer or atomizer.

The compounds made according to the present invention can be used to treat warm blooded animals, birds, and mammals. Examples of such beings include humans, cats, dogs, horses, sheep, cows, pigs, lambs, rats, mice, and guinea pigs.

According to one aspect of the present invention, the piperidine derivative compounds are prepared by providing a regioisomer of the following formula:

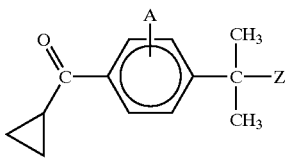

and converting the regioisomer to the piperidine derivative compounds of the invention having a keto group with a piperidine compound.

The resulting piperidine derivative compounds with a keto group can then be converted by reduction to the above-described piperidine compounds with a hydroxyl group.

A is the substituents of its ring, each of which may be different or the same and is selected from the group consisting of hydrogen, halogens, alkyl, hydroxy, alkoxy, or other substituents.

Z can be a carbon atom to which are bonded three electron rich groups, such as moieties having the formula $CG^1G^2G^3$. $G^1$, $G^2$, and $G^3$ can be the same or different and are illustratively selected from the group consisting of $OR^8$, $SR^8$, and $NR^8R^9$, where $R^8$ and $R^9$ arc the same or different and can be hydrogen; an alky,l moiety, including substituted or unsubstituted, branched or straight-clhain alkyl moieties, such as methyl, ethyl, n-propyl, isopropyl, n-butyl, sec-butyl, tert-butyl, n-pentyl, neopentyl, n-hexyl, benzyl, and 4-methylbenzyl, preferably having from 1 to 7 carbon atoms; or an aryl moiety, including substituted or unsubstituted aryl moieties, such as phenyl, tolyl, and xylyl. Examples of such a Z include triethoxymethyl or trimethoxymethyl moieties.

Z can also be a heterocyclic moiety having the formulae:

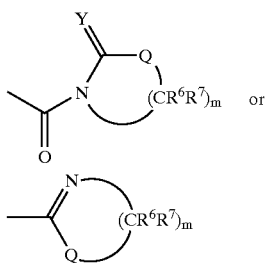

where m is an integer from 1 to 6 and Q and Y are independently oxygen, sulfur, or a substituted or unsubstituted amine having the formula $NR^5$. $R^5$ can be hydrogen; an alkyl moiety, including substituted or unsubstituted, branched or straight-chain alkyl moieties, such as methyl, ethyl, n-propyl, isopropyl, n-butyl, sec-butyl, tert-butyl, n-pentyl, neopentyl, n-hexyl, benzyl, and 4-methylbenzyl, preferably having from 1 to 7 carbon atoms; or an aryl moiety, including substituted or unsubstituted aryl moieties, such as phenyl, tolyl, and xylyl groups. It is to be understood that $R^6$ and $R^7$, the two substituents bonded to each methylene (i.e. $CH_2$ group), of which there are m in the above formulae, are independently selected from each other. In addition, it is to be understood that $R^6$ groups and $R^7$ groups on one methylene can be the same or different than those on other methylenes. Each $R^6$ and each $R^7$ can be hydrogen; an alkyl moiety, including substituted or unsubstituted, branched or straight-chain alkyl moieties, such as methyl, ethyl, n-propyl, isopropyl, n-butyl, sec-butyl, tert-butyl, n-pentyl, neopentyl, n-hexyl, 2-methylpentyl, cyclohexyl, benzyl, and 4-methylbenzyl, preferably having from 1 to 7 carbon atoms; an aryl moiety, including substituted or unsubstituted aryl moieties, such as phenyl, tolyl, xylyl, and naphthyl; or a moiety having the formulae $OR^8$, $SR^8$, or $NR^8R^9$, where $R^8$ and $R^9$ are defined as they were above where Z had the formula $CG^1G^2G^3$. Preferred examples of Z include isoxazoline moieties having the formula:

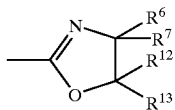

wherein $R^6$, $R^7$, $R^{12}$, and $R^{13}$ are the same or different and can be hydrogen; an alkyl moiety, including substituted or unsubstituted, branched or straight-chain alkyl moieties, such as methyl, ethyl, n-propyl, isopropyl, n-butyl, sec-butyl, tert-butyl, n-pentyl, neopentyl, n-hexyl, 2-methylpentyl, cyclohexyl, benzyl, and 4-methylbenzyl, preferably having from 1 to 7 carbon atoms; an aryl moiety, including substituted or unsubstituted aryl moieties, such as phenyl, tolyl, xylyl, and naphthyl; or a moiety having the formulae $OR^8$, $SR^8$, or $NR^8R^9$, where $R^8$ and $R^9$ are as defined as they were above. Preferably, m is 2, and $R^{12}$ and $R^{13}$ are hydrogen. More preferably, $R^{12}$ and $R^{13}$ are hydrogen, and $R^6$ and $R^7$ are each an alkyl moiety having from 1 to 7 carbon atoms. Most preferably, Z is 4,4-dimethylisoxazolin-2-yl, where each of $R^{12}$ and $R^{13}$ is hydrogen and $R^6$ and $R^7$ is methyl.

A variety of methods can be used to provide these regioisomers.

Process For Producing The Regioisomer

In one embodiment of the present invention, the regioisomer is produced by acylating an α,α-disubstituted-methylbenzene derivative having the formula:

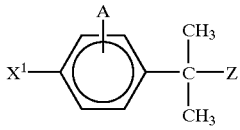

with a compound having the formula:

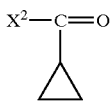

under conditions effective to produce the regioisomer having the formula:

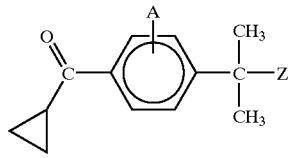

In this embodiment, the acylation agent is a cyclopropyl derivative.

In another embodiment of the present invention, the acylation agent is a 4-(α,α-disubstituted)-toluic acid derivative. In this embodiment, the regioisomer is produced by reacting a 4-(α,α-disubstituted)-toluic acid derivative having the formula:

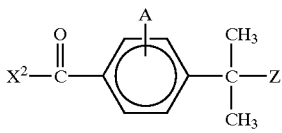

with a compound having the formula:

under conditions effective to acylate the compound, producing the regioisomer.

Irrespective of whether the regioisomer is produced using the process employing a cyclopropyl derivative acylation agent or the process employing a 4-((α,α-disubstituted)-toluic acid derivative acylation agent, $X^1$ can be a halogen; trialkyl or triaryl tin; trialkyl or triaryl borate; alkylhalo silicon; trialkyl silicon; or a substituted sulfonic ester, such as tosylate, mesylate, or triflate, with any alkyl groups being straight or branched and preferably having 1 to 4 carbon atoms. Alternatively, $X^1$ can be a substituent usefull in organometallic coupling reactions, including lithium or magnesium compounds derived from bromine or iodine. As used herein, alkylhalo silicon is a tetravalent silicon atom bonded to at least one halogen and at least one alkyl group. The remaining silicon valency is bonded to either a second halogen or a second alkyl. One particularly useful alkylhalo silicon has the formula —$SiCH_3F_2$.

$X^2$, in either embodiment, can be hydrogen; a halogen; an alkali metal oxide; a moiety having the formula —$OR^{10}$; a moiety having the formula —$SR^{10}$; or an amine. Suitable amines are those having the formula —$NR^{10}R^{11}$ or —$NR^{10}(OR^{11})$; saturated cyclic amines, such as those having the formnulae:

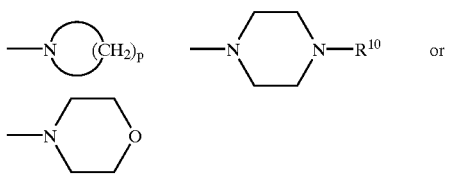

or heteroaryl amines, such as imidazole, pyrazole, and the like. $R^{10}$ and $R^{11}$ are the same or different and are selected from the group consisting of hydrogen; an alkyl moiety, including substituted or unsubstituted, branched or straight-chain alkyl moieties, such as methyl, ethyl, n-propy,l, isopropyl, n-butyl, sec-butyl, tert-butyl, n-pentyl, neopentyl, n-hexyl, benzyl, and 4-methylbenzyl, preferably having from 1 to 7 carbon atoms; and an aryl moiety, including substituted or unsubstituted aryl moieties, such as phenyl, tolyl, and xylyl groups; p is an integer, preferably from 2 to 8.

In practicing the process employing a cyclopropyl derivative acylation agent, suitable acylation agents include cyclopropylcarboxylic acid halides, alkali metal cyclopropylcarboxylic acid salts, cyclopropylcarboxylic acid esters, or cyclopropylcarboxylic acid amides.

Suitable cyclopropylcarboxylic acid halides include cyclopropylcarboxylic acid fluoride, cyclopropylcarboxylic acid chloride, and cyclopropylcarboxylic acid bromide. Where an alkali metal salt of cyclopropylcarboxylic acid is employed as the acylation agent, suitable alkali metals include lithium, sodium, and potassium.

Cyclopropylcarboxylic acid amides can be N-unsubstituted amides, such as cyclopropylcarboxylic acid amide; an N-monosubstituted amide, such as N-methyl cyclopropylcarboxylic acid amide, N-ethyl cyclopropylcarboxylic acid amide, N-propyl cyclopropylcarboxylic acid amide, and N-hexyl cyclopropylcarboxylic acid amide; or an N,N-disubstituted amide. Suitable N,N-disubstituted amides include N,N-dimethyl cyclopropylcarboxylic acid amide, N-methyl-N-ethyl cyclopropylcarboxylic acid amide, N-methyl-N-propyl cyclopropylcarboxylic acid amide, N-methyl-N-hexyl cyclopropylcarboxylic acid amide, N,N-diethyl cyclopropylcarboxylic acid amide, N-ethyl-N-propyl cyclopropylcarboxylic acid amide, N-ethyl-N-hexyl cyclopropylcarboxylic acid amide, N,N-dipropyl cyclopropylcarboxylic acid amide, N-propyl-N-hexyl cyclopropylcarboxylic acid amide, and N,N-dihexyl cyclopropylcarboxylic acid amide. N,N-disubstituted cyclopropylcarboxylic acid amides having the formula —$NR^{10}(OR^{11})$, such as N-methyl-N-methoxy cyclopropylcarboxylic acid amide, N-methyl-N-ethoxy cyclopropylcarboxylic acid amide, N-ethyl-N-methoxy cyclopropylcarboxylic acid amide, and N-ethyl-N-ethoxy cyclopropylcarboxylic acid amide, are particularly useful. Suitable N,N-disubstituted amides also include cyclic amides, such as cyclopropyl carboxylic acid morpholine amide, cyclopropyl carboxylic acid piperazine amide, cyclopropyl carboxylic acid imidazole amide, and cyclopropyl carboxylic acid pyrazole amide, as well as those having the formula:

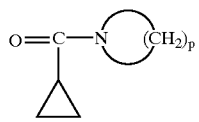

where p is an integer, preferably from 2 to 8, examples of which include N,N-ethylene cyclopropylcarboxylic acid amide, N,N-propylene cyclopropylcarboxylic acid amide, N,N-butylene cyclopropylcarboxylic acid amide, and N,N-pentylene cyclopropylcarboxylic acid amide.

Irrespective of whether the regioisomer is produced using the process employing a cyclopropyl derivative acylation agent or the process employing a 4-(α,α-disubstituted)-toluic acid derivative acylation agent, the acylation reactions are carried out in a suitable solvent in the presence of an appropriate catalyst for about I to 120 hours and at temperatures of about −78° C. to the reflux temperature of the solvent. Suitable solvents for acylation include: hydrocarbon solvents, such as benzene, toluene, xylene, or cyclohexane; halogenated hydrocarbons, such as chlorobenzene, dichloroethane, methylene chloride, chloroform, or carbon tetrachloride; carbon disulfide; dimethylformamide; ethereal solvents, like tetrahydrofuran and diethylether; or dioxane.

In practicing either of the above processes, a variety of catalysts may be utilized when A is hydrogen. Suitable catalysts include palladium catalysts, like palladium chloride, palladium acetate, tetrakis(triphenylphosphine) palladium(0), dichlorobis(triphenylphosphine) palladium (II), or benzylchlorobis(triphenylphosphine)palladium(II); or nickel-phosphine catalysts. Acylation may also be carried out in the presence of added lithium chloride or triphenylphosphine. The latter acylation reaction is known in the art as organometallic cross-coupling reactions and are conducted by the general procedures of D. Milstein, et al., *J. Org. Chem.*, 1979, 44, 1613; J. W. Labadie, et al., *J. Org. Chem.*, 1983, 48, 4634. C. Salilberg, et al., *Tetrahedron Letters*, 1983, 24, 5137; D. Milstein, et al., *J.Am. Chem. Soc.*, 1978, 100, 3636; and K. Tamao, et al., *Tetrahedron*, 1982, 38, 3347, all of which are hereby incorporated by reference.

Where acylation is ca ied out using the process employing a cyclopropyl derivative acylation agent, the reaction can also be promoted by addition of an acylation promoter which, when reacted with the mcthylbenzene derivative, displaces $X^1$ from the benzene ring, forming a reactive carbanion salt. One suitable acylation promoter is butyl lithium, which is particularly effective when $X^2$ is an amine. When $X^2$ is chloride, preferred acylation promoters are magnesium metal or tetraalkyl tin. Acylation promoters, especially organometallics such as butyl lithium, are highly reactive with carbonyl groups. For this reason, the Z moiety is chosen to minimize reactivity of the carbon beta to the benzene ring. In particular, when employing an acylation promoter, Z moieties having the formula:

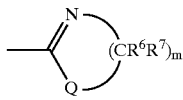

such as isoxazolidium groups, are preferred.

The α,α-disubstituted-methylbenzene derivative having the formula:

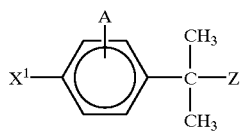

can be provided by reacting an α,α-diunsubstituted-methylbenzene derivative having the formula:

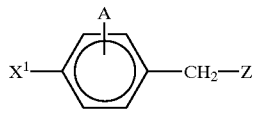

with a methylating agent under conditions effective to produce the α,α-disubstituted-methylbenzene derivative. The methylation reaction is carried out in a suitable solvent and in the presence of a suitable non-nucleophilic base, such as potassium t-butoxide, sodium hydride, lithium diisopropylamide ("LDA"), lithium hexamethyldisilazide ("LHMDS"), potassium hexamethyldidisilazide ("KHMDS"), sodium or lithium tetramethylpiperidine, or related strong bases, for about 1 to about 120 hours, at temperatures from about −78° C. to room temprature. Preferably, the reaction is conducted under an inert, dry atmosphere, such as $N_2$ or Ar gas, in an inert, dry solvent. Suitable solvents for methylation include: hydrocarbon solvents, such as benzene, toluene, xylene, or cyclohexane; halogenated hydrocarbons, such as chlorobenzene, dichloroethane, methylene chloride, or carbon tetrachloride; carbon disulfide; dimethylformamide; ethereal solvents, like tetrahydrofuran, t-butyl methyl ether, and diethylether; or dioxane. At least two molar equivalents and, preferably, between 2.1 and 3 molar equivalents of methylating agent are employed and added over the course of the reaction, either continuously or in two or more slugs. Suitable methylating agents include iodomethane, bromomethane, chloromethane, dimethyl sulfate, and the like.

The α,α-diunsubstituted-methylbenzene derivatives having the formula:

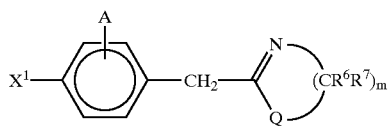

can be prepared by reacting the correponding α,α-diunsubstituted benzylic acid of the formula:

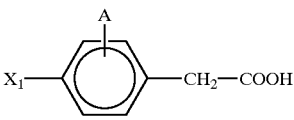

with an appropriate aminoalkyl derivative having the formula:

under conditions effective to produce the α,α-diunsubstituted-methylbenzene derivative. This reaction is conducted in a suitable solvent for about 1 to about 120 hours and at a temperature ranging from 0° C. to the reflux temperature of the solvent. Suitable solvents for this reaction include: hydrocarbon solvents, such as benzene, toluene, xylene, or cyclohexane; halogenated hydrocarbons, such as chiorobenzene, dichlorethane, methylene chloride, chloroform, or carbon tetrachloride; carbon disulfide; dimethylformamide; etheral solvents, like tetrahydrofuran and diethylether; or dioxane. Preferably, the solvent is maintained at reflux in an apparatus having a means for removing water, such as a Dean-Stark trap. In many cases, it is advantageous to convert the (α,α-diunsubstituted-benzylic acid derivative to the corresponding acid halide, such as by treatment with thionyl chloride, prior to reaction with the aminoalkyl derivative.

Alternatively, the α,α-disubstituted-methylbenzene derivative having the formula:

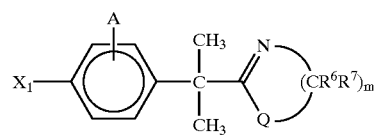

can be prepared from the corresponding α,α-disubstituted-benzylic acid derivative having the formula:

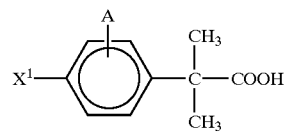

by reacting the α,α-disubstituted-benzylic acid derivative with the above aminoalkyl derivative under the conditions described above with respect to the α,α-diunsubstituted-benzylic acid conversion.

The α,α-disubstituted-benzylic acid derivative used to prepare the α,α-disubstituted-methylbenzene derivative can be synthesized by methylating the corresponding α,α-diunsubstituted-benzylic acid derivative. Conditions suitable to carry out this methylation are the same as those described above with respect to methylation of α,α-diunsubstituted-methylbenzene derivatives.

Where acylation is carried out with a 4-(α,α-disubstituted)-toluic acid derivative having the formnula:

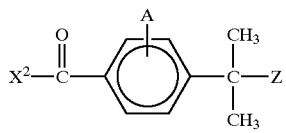

the 4-(α,α-disubstituted)-toluic acid derivative can be provided by reacting a 4-(α,α-diunsubstituted)-toluic acid derivative having the formula:

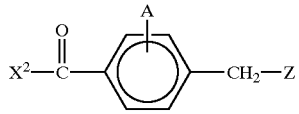

with a methylating agent under conditions effective to produce the 4-(α,α-disubstituted)-toluic acid derivative. Suitable methylation conditions are the same as those described above. The 4-(α,α-diunsubstituted)-toluic acid derivatives having the formula:

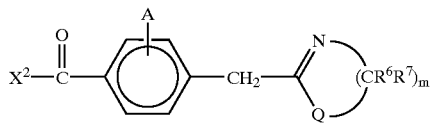

can be prepared by reacting the correponding 4-(α-carboxy-α,α-diunsubstituted)-toluic acid derivative having the formula:

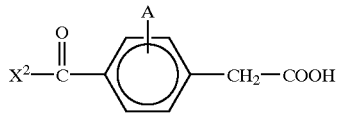

with an appropriate aminoalkyl derivative having the formula:

under conditions effective to produce the 4-(α,α-diunsubstituted)-toluic acid derivative. Conditions suitable to effect this reaction are the same as those given above for reaction of α,α-diunsubstituted-methylbenzene derivatives with aminoalkyl derivatives.

Alternatively, the 4-(α,α-disubstituted)-toluic acid derivative having the formula:

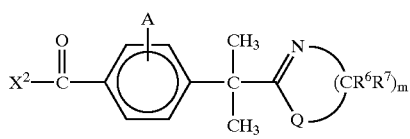

can be prepared from the corresponding 4-(α-carboxy-α,α-disubstituted)-toluic acid derivative having the formula:

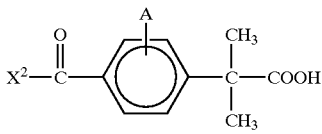

by reacting the 4-(α-carboxy-α,α-disubstituted)-toluic acid derivative with the above aminoalkyl derivative under the conditions described above with respect to the reaction of α,α-diunsubstituted-benzylic acid derivatives with aminoalkyl derivatives.

The 4-(α-carboxy-α,α-disubstituted)-toluic acid derivative used to prepare the 4-(α,α-disubstituted)-toluic acid derivative can be synthesized by methylating the corresponding 4-(α-carboxy-α,α-diunsubstituted)-toluic acid derivative. Conditions suitable for carrying out this methylation are the same as those described above with respect to methylation of α,α-diunsubstituted-methylbenzene derivatives.

The regioisomer of the present invention having the formula:

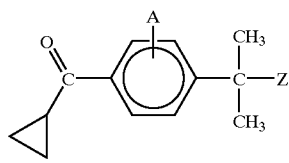

can also be prepared from a corresponding (α,α-diunsubstituted regioisomer precursor having the formula:

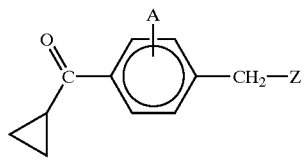

by methylation using reagents and conditions described above with respect to the methylation of α,α-diunsubstituted-methylbenzene derivatives. When employing this route, the (α,α-diunsubstituted regioisomer precursor is conveniently prepared from a (α,α-diunsubstituted-methylbenzene derivative having the formnula:

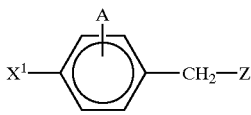

by acylating the α,α-diunsubstituted-methylbenzene derivative with an acylation agent having the formula:

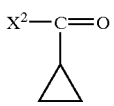

under conditions effective to produce the α,α-diunsubstituted regioisomer precursor. Acylation conditions suitable for this reaction are the same as those described above with respect to acylation of α,α-disubstituted-methylbenzene derivatives.

Process Of Converting The Regioisomer to The Piperidine Derivative Having A Keto Group Once the regioisomer is provided, it is then converted to the piperidine derivative with a piperidine compound.

In one aspect of the invention, the regioisomer having the formula:

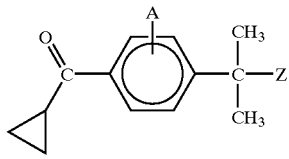

is reacted with a piperidine compound having the formula:

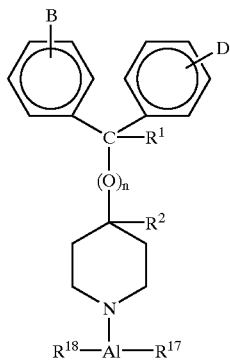

$R^{17}$ and $R^{18}$ in the above formnula can be the same or different and are selected from the group consisting of an alkyl moiety, including substituted or unsubstituted, branched or straight-chain alkyl moieties, such as methyl, ethyl, n-propyl, isopropyl, n-butyl, sec-butyl, tert-butyl, n-pentyl, neopentyl, n-hexyl, benzyl, and 4-methylbenzyl, preferably having from 1 to 7 carbon atoms; and an aryl moiety, including substituted or unsubstituted aryl moieties, such as phenyl, tolyl, and xylyl groups. Preferably, the reaction is conducted under an inert, dry atmosphere, such as nitrogen or argon, in an inert, dry solvent, at temperatures from about −50 ° C. to about the reflux temperature of the solvent. Suitable solvents include hydrocarbon solvents, such as benzene, toluene, xylene, or cyclolhexane; dimethylformarnmide; ethereal solvents, like tetrahydrofuran, t-butyl methyl ether, and diethylether; or dioxane.

In another aspect of the present invention, conversion of the regioisomer to the piperidine derivative is effected by halogenating, hydroxylating, alkoxylating, or aryloxylating the regioisomer under conditions effective to form a first intermediate compound having the formula:

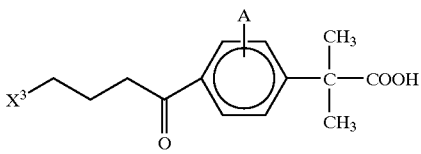

wherein $X^3$ is a halogen or a hydroxy, alkoxy, or aryloxy moiety.

Suitable halogens include chlorine, bromine, and iodine. Suitable conditions for carrying out halogenating include reacting the regioisomer with a halogen nucleophile and a Lewis Acid. The halogenation reaction is carried out in a suitable solvent, optionally in the presence of a catalytic amount of base, for about 0.5 to 24 hours and a temperature of about −40 degrees C. to the reflux temperature of the solvent. Suitable halogen nucleophiles include sodium iodide, sodium bromide, potassium iodide, potassium bromide, cesium iodide. cesium bromide, trimethylsilyl iodide, manganese iodide, cerium iodide, magnesium bromide, magnesium iodide, magnesium carbonate, calcium bromide, and calcium iodide. Suitable Lewis Acids include silicon compounds, such as trimethylsilyl chloride and trimethylsilyl iodide; aluminum compounds, such as aluminum chloride, trimethyl aluminum, diethyl aluminum chloride, ethyl aluminum dichloride, and diethyl aluminum cyanide; magnesium salts; and boron salts. Suitable solvents for the halogenation reaction include alcohols, such as methanol, ethanol, isopropanol, and various glycols; hydrocarbon solvents, such as, benzene, toluene, xylene, or cyclohexane; ethereal solvents such as ether, tetrahydrofuran, dioxane, or dimethoxyethane; or halogenated hydrocarbons, such as, chlorobenzene, methylene chloride, carbon tetrachloride, chloroform, or dichloroethane.

The halogenation reaction can be conducted in a mixture of organic solvent and mineral acid, such as hydrochloric acid, hydrobromic acid, or hydroiodic acid. In this manner, in addition to decyclizing the cyclopropyl ring, the moiety herein referred to as Z is cleaved, yielding the first intermediate compound.

Alternatively, the above halogenation can comprise two separate steps. In the first step, the regioisomer of the present invention is decyclized under conditions effective to produce an oxobutyl derivative having the formula:

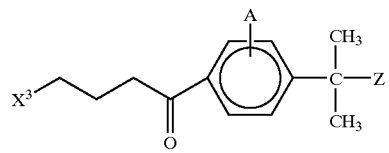

Decyclizing can be effected with a halogen nucleophile and a Lewis Acid under conditions described above. At this point, the oxobutyl derivative can optionally be purified to remove excess decyclizing reagent. The oxobutyl derivative is converted to the first intermediate compound by treatment of the oxobutyl derivative with a mineral acid, such as hydrochloric acid, hydrobromic acid, or hydroiodic acid. It is preferred that treatment with acid be effected separately from the decyclizing. Further, it is preferred that treatment with acid be effected on purified oxobutyl derivative, rather than on oxobutyl derivative contaminated with excess decyclizing agent.

As indicated above, the regioisomer can also be converted to the oxobutyl derivative by hydroxylation, alkoxylation, or aryloxylation. In such cases, $X^3$ is $OR^{19}$, where $R^{19}$ can be hydrogen, an alkyl group, or an aryl group. Alkoxylation or aryloxylation is carried out by reacting the regioisomcr with mineral acids in an solution of the appropriate alcohol, such as methanol when $R^{19}$ is methyl, ethanol when $R^{19}$ is ethyl, and phenol when $R^{19}$ is phenyl. Hydroxylation can be effected by treating the regioisomer with mineral acids in an aqueous solution. The intermediate hydroxy compound can then be converted to a sulfonate ester, such as the tosylate or mesylate ester, by reaction with a sulfonyl halide, such as p-toluenesulfonyl chloride or methanesulfonyl chloride.

If desired, the acid group of the first intermediate compound can be esterified by techniques well known to those skilled in the art, such as by evaporating an alcoholic solution of the acid and a mineral acid, such as a methanolic, ethanolic, propanolic, or butanolic solution of hydrochloric, hydrobromic, or hydroiodic acid, to dryness to form an ester having the formula:

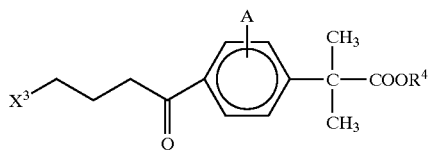

After halogenation, alkoxylation, or aryloxylation and optional esterification, the first intermediate compound or ester thereof can be reacted with a piperidine compound of the formula:

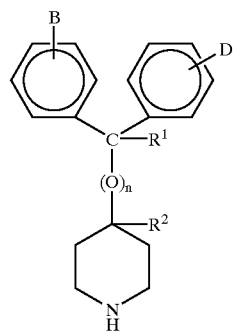

under conditions effective to form the piperidine derivative compound having a keto group of the formula:

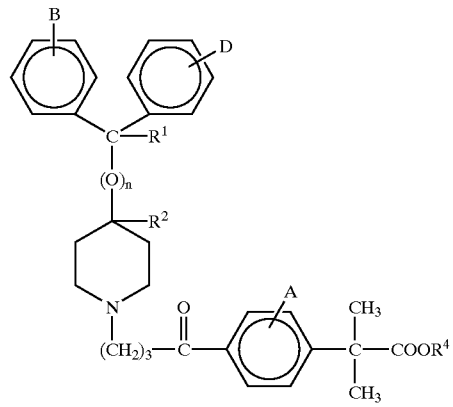

This alkylation reaction is carried out in a suitable solvent preferably in the presence of a base and, optionally, in the presence of a catalytic amount of potassiumi iodide for about 4 to 120 hours at a temperature of about 70° C. to the reflux temperature of the solvent. Suitable solvents for the alkylation reaction include alcohol solvents, such as, methanol, ethanol, isopropyl alcohol, or n-butanol; ketone solvents, such as methyl isobutyl ketone and methyl ethyl ketone; hydrocarbon solvents, such as benzene, toluene, or xylene; halogenated hydrocarbons, such as, chlorobenrzene or methylene chloride; or dimethylformamide. Suitable bases for the alkylation reaction include inorganic bases, for example, sodium bicarbonate, potassium carbonate, or potassium bicarbonate or organic bases, such as a trialkylamine, for example, triethylamine or pyridine, or an excess of the piperidine compound can be used. When the piperidine derivative is in the form of an ester, it can be hydrolyzed to a carboxylic acid.

Piperidine derivative compounds of the present invention having n equal to 1 can also be prepared by the following alternative alkylation procedure. Subsequent to halogenation and optional esterification, the first intermediate compound having the formula:

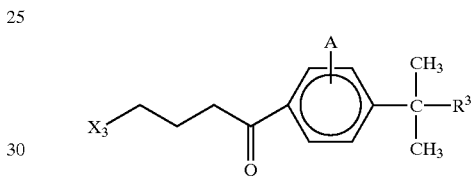

is reacted with 4-hydroxypiperidine in an organic solvent, such as toluene, dioxane, xylene, methyl ethyl ketone, methyl isobutyl ketone, or N,N-dimethylformamide, at a temperature between 80° and 140° C. and in the presence of an acid-binding agent, such as an alkali metal carbonate or bicarbonate, to form an N-substituted hydroxypiperidine having the formula:

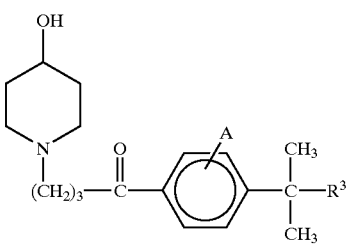

The N-substituted hydroxypiperidine is then reacted with a diphenylmonohalomethane having the formula:

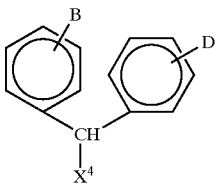

wherein $X^4$ is a halogen, under conditions effective to form the piperidine derivative compound of the formula:

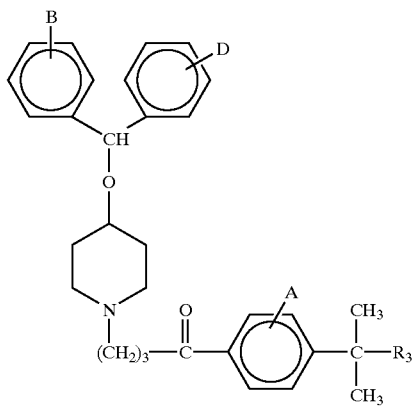

The reaction is preferably carried out in an inert organic solvent, for example, toluene, xylene, dioxane, methyl isobut,l ketone, or N,N-dimethylformamide, at a temperature between 80° and 140° C. in the presence of an acid-binding agent such as an alkali metal carbonate or bicarbonate. The diphenylmonohalomethanes can be obtained commercially, or they can be prepared by the methods known in the art, for example, by reaction of the corresponding diphenylmethanol with a phosphorous or thionyl chloride or bromide in an inert organic solvent. This alternative alkylation method is preferred when $R^3$ in the first intermediate compound is —COOH.

Irrespective of the alkylation procedure employed, when $R^3$ is —COOalkyl, the alkylation reaction can be followed by base hydrolysis to convert $R^3$ substituents that are —COOalkyl groups to —COOH groups. Such base hydrolysis involves treatment of the piperidine derivative with an inorganic base, such as sodium hydroxide, in an aqueous lower alcohol solvent, such as aqueous methanol, ethanol, isopropyl alcohol, or n-butanol, at reflux temperature for about ½ hour to 12 hours.

Piperidine compounds where n=0 and each of $R^1$ and $R^2$ is hydrogen or where n=0 and $R^1$ is hydroxy and $R^2$ is hydrogen are commercially available or may be prepared according to procedures well known in the art (e.g. F. J. McCarty, C. H. Tilford, M. G. Van Campen, *J. Am. Chem. Soc.*, 1961, 26, 4084, which is hereby incorporated by reference). Piperidine compounds wherein n=0 and $R^1$ and $R^2$ form a second bond between the carbon atoms bearing $R^1$ and $R^2$ may be prepared by dehydration of the corresponding compound wherein $R^1$ is hydroxy by procedures generally known in the art. Piperidine compounds wherein n=1 and $R^1$ and $R^2$ are both hydrogen are prepared by condensation of an appropriately substituted diphenylmonohalomethane, such as diphenylchloromethane, diphenylbromomethane, and di(p-tolyl)chloromethane, with a 1-alkoxycarbonyl-4-hydroxypiperidine in a suitable solvent, such as toluene, xylene, dioxane, methyl isobutylketone, or N,N-dimethylformamide. The reaction is conducted at a temperature between 80° C. and 140° C. and in the presence of a base, such as an alkali metal carbonate or bicarbonate. Following the reaction, hydrolysis with alkali metal hydroxide in an organic solvent, such as ethanol or isopropanol, at the boiling point of the solvent, yields the 4-(diarylmethoxy)-piperidine free base.

In yet another aspect of the present invention, the piperidine derivative compound is produced by decyclizing the regioisomer of the present invention under conditions effective to produce a oxobutyl derivative compound having the formula:

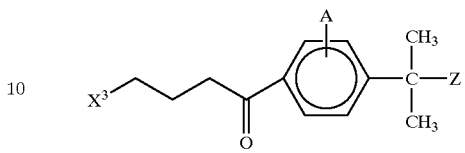

Decyclization can be effected by reacting the regioisomer with a halogen nucleophile and a Lewis Acid. Decyclization is carried out in a suitable solvent, optionally in the presence of a catalytic amount of an optional nucleophile, for about 0.5 to 24 hours and a temperature of about −40 degrees C to the reflux temperature of the solvent. Suitable halogen, Lewis Acids, and solvents include those which were discussed above in regard to halogenating the regioisomer.

The oxobutyl derivative compound is converted to a piperidine derivative precursor having the formula:

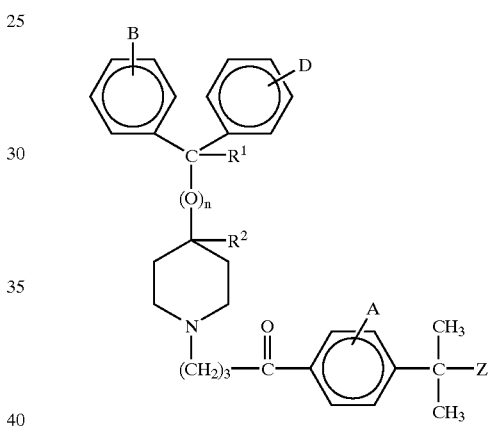

by reacting the oxobutyl derivative with a piperidine compound having the formula:

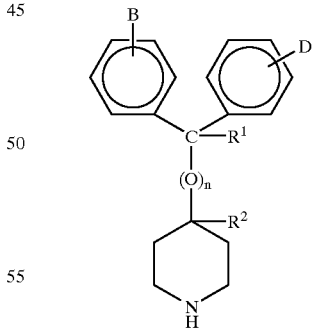

under conditions effective to form the piperidine derivative precursor. This alkylation reaction is carried out in a suitable solvent preferably in the presence of a base and, optionally, in the presence of a catalytic amount of potassium iodide for about 4 to 120 hours at a temperature of about 70° C. to the reflux temperature of the solvent. Suitable solvents for the alkylation reaction include alcohol solvents, such as, methanol, ethanol, isopropyl alcohol, or n-butanol; ketone solvents, such as, methyl isobutyl ketone and methyl ethyl ketone; hydrocarbon solents, such as, benzene, toluene, or xylene; halogenated hydrocarbons, such as, chlorobenzene or methylene chloride; or dimethylformamnide. Suitable bases for the alkylation reaction include inorganic bases, for example, sodium bicarbonate, potassium carbonate, or potassium bicarbonate or organic bases, such as a trialkylamine, for example, triethylamine or pyridine, or an excess of the piperidine compound can be used.

Alternatively, piperidine derivative precursors of the present invention having n equal to 1 can also be prepared by reacting the oxobutyl derivative having the formula:

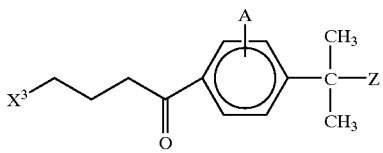

with 4-hydroxypiperidine in an organic solvent, such as toluene, dioxane, xylene, methyl isobutyl ketone, or N,N-dimethylformamide, at a temperature between 80° and 140° C. and in the presence of an acid-binding agent, such as an alkali metal carbonate or bicarbonate, to form an N-substituted hydroxypiperidine having the formula:

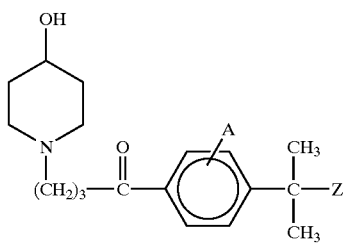

The N-substituted hydroxypiperidine is then reacted with a diphenylmonohalomethane having the formula:

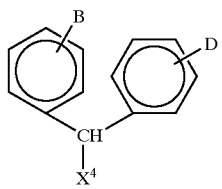

wherein $X^4$ is a halogen, under conditions effective to form the piperidine derivative precursor of the formula:

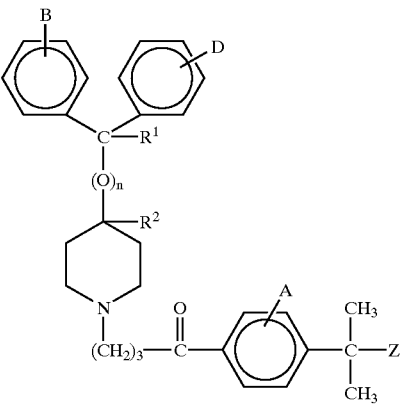

The reaction is preferably carried out in an inert organic solvent, for example, toluene, xylene, dioxane, methyl isobutyl ketone, or N,N-dimethylformamide, at a temperature between 80° and 140° C. in the presence of an acid-binding agent such as an alkali metal carbonate or bicarbonate.

Irrespective of the alkylation procedure employed, the piperidine derivative precursor is then converted to the piperidine derivative having the formula:

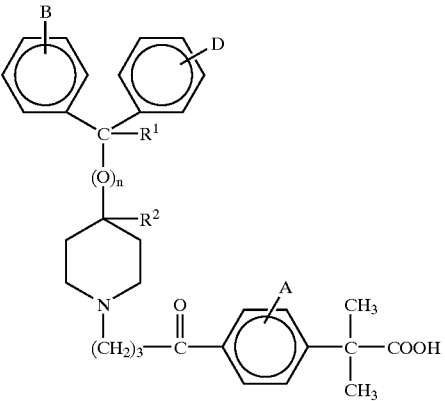

This conversion can be effected by treatment of the piperidine derivative precursor with a mineral acid, such as hydrochloric acid, hydrobromic acid, or hydroiodic acid in a suitable organic solvent, for about 0.5 to 24 hours and a temperature of about –40 degrees C. to the reflux temperature of the solvent. Suitable solvents include alcohols, such as methanol, ethanol, isopropanol, and various glycols; hydrocarbon solvents, such as, benzene, toluene, xylene, or cyclohexane; ethereal solvents such as ether, tetrahydrofuran, dioxane, or dimethoxyethane; or halogenated hydrocarbons, such as, chlorobenzene, methylene chloride, carbon tetrachloride, chloroform, or dichloroethane. Alternatively, this conversion can be effected in vivo by administering the piperidine derivative percursor to a subject, and permitting the subject to metabolize the piperidine derivative precursor to the piperidine derivative compound.

Piperidine derivative precursors of the present invention can be used to treat patients suffering from allergic reactions, such as asthma, allergic rhinitis, and other conditions which can be treated with piperidine derivative compounds. Treatment includes administering to the patient an effective amount of the piperidine derivative precursor. The amounts and modes of administration are the same as those discussed above for administration of piperidine derivative compounds.

Processes for Reduction of Keto Group in Piperidine Derivative Compounds and Precursors As discussed above, the process of the present invention is useful in producing piperidine derivatives with either a keto group or a hydroxyl group. Derivatives with keto groups can be converted to similar compounds with hydroxyl groups by reduction reactions which are well known in the art.

Reduction can be carried out with sodium borohydride or potassium borohydride in lower alcohol solvents, such as, methanol, ethanol, isopropyl alcohol, or n-butanol.

When lithium aluminum hybride or diborane are used as reducing agents, suitable solvents are ethers, for example, diethyl ether, tetrahydrofuran, or dioxane. These reduction reactions are carried out at temperatures ranging from about 0° C. to the reflux temperature of the solvent, and the reaction time varies from about 0.5 to 8 hours.

Catalytic reduction with hydrogen may also be employed using, for example, Raney nickel, palladium, platinum, or rhodium catalysts in lower alcohol solvents, such as, methanol, ethanol, isopropyl alcohol, or n-butanol or acetic acid or their aqueous mixtures, or by the use of aluminum isopropoxide in isopropyl alcohol. Reduction using sodium borohydride is generally preferred over catalytic reduction when forming carboxylic acids or esters.

The piperidine derivative containing a hydroxy group thus prepared can optionally be separated into its enantiomerically pure components by conventional methods. For example, the racemic mixture of piperidine derivative enantiomers can be converted to a racemic mixture of diastereomers with a reactive chiral agent. The diastereomers are then separated by, for example, recrystallization or chromatography, and the pure enantiomer is recovered by cleaving the reactive chiral agent. Alternatively, the racemic mixture of piperidine derivative enantiomers can be chromatographically separated using chiral stationary phases or by recrystallization by usinq chiral solvents.

Piperidine derivatives having keto groups can also be converted to enantiomerically pure piperidine derivatives having hydroxy groups by using chiral reducing agents. For example, reduction using (+)-B-chlorodiisopropinocamphenylborane produces the piperidine derivative having R chirality at the carbon to which the hydroxy group is bonded. Alternatively, by using (−)-B-chlorodiisopropinocamphenylborane produces the S enantiomer. Other suitable chiral reducing agents are (R) and (S)-oxazaborolidine/$BH_3$, potassium 9-O-(1,2:5,6-di-O-isopropylidine-α-D-glucofuransoyl)-9-boratabicyclo [3.3.1] nonane, (R) and (S)-B-3-pinanyl-9-borabicyclo[3.3.1] nonane, NB-enantride, lithium (R)-(+) and (S)-(−)-2,2'-dihydroxy-1,1'-binaphthyl alkoxyl aluminum hydride, (R)-(+)-and (S)-(−)-2,2'-dihydroxy-6,6'-dimethylbiphenyl borane-amine complex, tris(((1S, 2S, 5R)-2-isoprophy-5-methyl-cyclohex-1-yl)methyl)aluminum, (((1R, 3R)- 2,2-dimethylbicyclo[2.2.1]hept-3-yl)methyl)beryllium chloride, (R)-BINAP-ruthenium complex/$H_2$, and 6,6'-bis (diphenylphosphino)-3,3'-dimethoxy-2,2',4,4'-tetramethyl-1,1'-biphenyl.

When esters with hydroxyl groups have been formed, base hydrolysis can be used to produce a carboxylic acid. Such procedures are well known and generally involve treatment with an inorganic base, such as, sodium hydroxide or potassium hydroxide, in an aqueous lower alcoholic solvent, such as aqueous methanol, ethanol, isopropyl alcohol, or n-butanol. Base hydrolysis is carried out at a temperature from about room temberature to about the solvent reflux temperature for about ½ hour to 12 hours.

In like manner, piperidine derivative precursors bearing a keto group and having the formula:

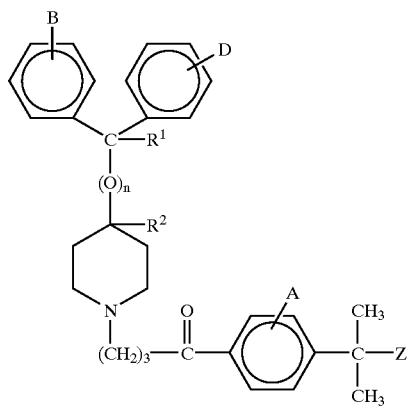

can be reduced to piperidine derivative precursors bearing a hydroxyl group having the formula:

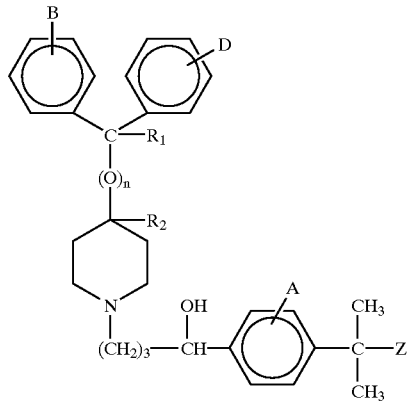

The piperidine derivative precursors bearing a hydroxyl group can be converted to the piperidine derivative having the formula:

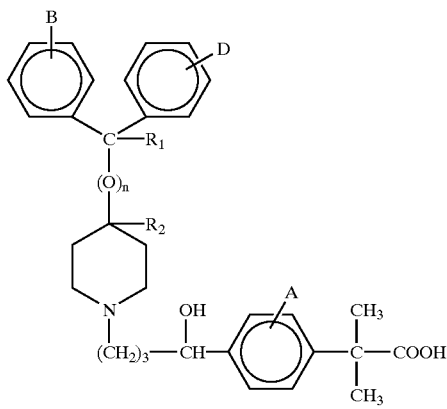

in vitro, such as by treating the piperidine derivative precursor bearing a hydroxyl group with strong acid, as discussed above, or, alternatively, in vivo, by administering the piperidine derivative precursor bearing a hydroxyl group to a subject. Piperidine derivative precursors bearing hydroxyl cyroups, like piperidine derivative precursors bearing keto groups, can be used to treat allergic reactions, such as asthma or allergic rhinitis.

The present invention is further illustrated by the following examples.

EXAMPLES

Example 1

Preparation of 4-Bromo-α-(4,4-dimethylisoxazolin-2-yl)toluene

A mixture of 4-bromophenylacetic acid (172 g, 0.800 mole), 2-amino-2-methyl-1-propanol (115 mL, 1.20 mole), and 900 mL xylenes were refluxed for 24 hours in an apparatus equipped with a Dean-Stark trap. The mixture was then cooled, filtered, and concentrated to afford a crystalline solid. The solid was slurried in hexanes, and filtered to afford 147 g of a white solid. The hexane filtrate was then concentrated, slurried with hexanes, and filtered to afford another 13 g of 4-bromo-α-(4,4-dimethylisoxazolin-2-yl) toluene as a white solid. The combined yield was 160 g (75%).

Example 2

Preparation of 4-Bromo-α,α-dimethyl-α-(4,4-dimethylisoxazolin-2-yl)toluene

A 250 mL three neck round bottomed flask was charged with 5.0 g (0.0186 mole) of 4-bromo-α-(4,4-dimethylisoxazolin-2-yl)toluene, prepared according to Example 1, and 50 mL of dry THF under $N_2$. KHMDS, 27 mL (0.0279 mole, 1.5 eq), was then slowly added over 10 minutes. A color change to deep orange was observed. After stirring the mixture for 15 minutes at room temperature, 1.16 mL (0.0186 mole, 1 equiv.) of methyl iodide was added in one portion. The reaction exothermned to 46° C., and white solid precipitated while the solution retained a pale yellow tint. After stirring for 1 hour, another 27 mL (0.0279 mole, 1.5 equiv.) of KHMDS was added causing the temperature of the reaction to rise from 27° to 30° C. and the color to change to orange. The reaction was stirred for an additional 20 minutes and, thereafter, a second equivalent of $CH_3I$ was added. An aliquot was removed, quenched with water, and extracted with ethyl acetate. TLC analysis (4:1 hexane/ethyl acetate) showed the presence of the more polar 4-bromo-α-methyl-α(4,4-dimethylisoxazolin-2-yl)toluene ("mono adduct"). An additional 0.2 mL of $CH_3I$ was added which turned the pale yellow solution to white. The reaction mixture was then added to 100 mL 10% acetic acid/water along with 250 mL methylene chloride. The organic layer was washed twice with 50 mL brine and dried with sodium sulfate. After concentration and drying at room temperature and a pressure of 0.1 mm Hg overnight, 5.65 g (103%) of a yellowish solid was obtained. The solid was dissolved in 30 mL isopropanol and 20 mL of water was slowly added until an oil had formed. To the mixture, 5 mL of isopropanol was added with heating to dissolve all of the oil. The oil crystallized upon cooling in an ice bath, yielding 4.61 g (0.0156 mniole, 84%) of pure 4-bromo-α,α-dimethyl-α-(4,4-dimethylisoxazolin-2-yl)toluene no trace of mono adduct.

Example 3

Preparation of 4-(Cyclopropyl-oxo-methyl)-α,α-dimethyl-α-(4,4-dimethyloxozolin-2-yl)toluene A solution of 4-bromo-α,α-dimethyl-α-(4,4-dimethlisoxazolin-2-yl)toluene, prepared according to Example 2, (10.0 g. 0.0338 mole) in 400 mL THF was cooled to −78° C., n-butyllithium (16 mL, 0.042 mole) was added via syringe, and the mixture was stirred at −78° C. for 30 minutes. While keeping the temperature below −75° C., N,N-dimethyl cyclopropylcarboxylic acid amide (11.5 g, 0.102 mole) in 30 mL THF was added dropwise, and the mixture was stirred at −78° C. for 30 minutes. The mixture was allowed to warm to −15° C., and was quenched with water. The product was extracted with methylene chloride, washed with saturated NaCl solution, dried over $Na_2SO_4$, and concentrated. The residue was cooled to 0° C., treated with minnimal acetonitrile, and filtered, to afford 6.95 g of 4-(cyclopropyl-oxo-methyl)-α,α-dimethyl-α-(4,4-dimethyloaozolin-2-yl)toluene as a white solid (72%).

Example 4

Preparation of 4-(4-Chloro-1-oxobutyl)-α,α-dimethlylphenylacetic Acid

A mixture of 4-(cyclopropyl-oxo-methyl)-α,α-dimethyl-α-(4,4-dimethyloxozolin-2-yl)toluene, prepared according to Example 3, (42 g, 0.15 mole), 150 mL concentrated hydrochloric acid, and 150 mL 1,4-dioxane was brought to reflux for 18 hours. The mixture was extracted three times with ethyl acetate. The organics vere washed with saturated NaCl solution, dried over $MgSO_4$, and concentrated. Crude product was purified by column chromatography using 240 g silica gel, and eluting with 81:14:5 hexanes/ethyl acetate/ acetic acid. Cleaner fractions were combined and recrystallized from methylene chloride/hexanes to afford 27 g of 4-(4-chloro-1-oxobutyl)-(α,α-dimcthylplienylacetic acid as a white solid (68%).

Example 5

Preparation of Methyl 4-(4-Chloro-1-oxobutyl)-α,α-dimethylphenylacetate

A solution of 4-(4-chloro-1-oxobutyl)-α,α-dimethylphenylacetic acid, prepared according to Example 4, (15 g, 0.056 mole) in 450 mL of a HCl-saturated methanol was refluxed for 1 hour. The mixture was concentrated to dryness and partitioned between ethyl acetate and water. The aqueous phase was extracted twice again with ethyl acetate. The combined organic phases were dried over $MgSO_4$ and concentrated to an oil. The oil was purified by column chromatography using 150 g of silica gel, and eluting with 11:1 hexanes/etlhyl acetate. Clean fractions were combined and concentrated to afford 13 g of methyl 4-(4-chloro-1-oxobutyl)-α,α-dimethylphenylacetate as a clear, colorless oil (82%).

Example 6

Preparation of Methyl 4-[4-[4-(Hydroxydiphenylmethyl)-1-piperidinyl]-1-oxobutyl]-α,α-dimethylphenylacetate A solution of 12.6 g of methyl 4-(4-chloro-1-oxobutyl)-α,α-dimethylphenylacetate in 500 mL of toluene in a one liter three neck flask with mechanical stirring was added 8.8 g of 4-(α,α-diphenyl)piperidinemethanol and 23 g of $K_2CO_3$ and the mixture was refluxed for 7 hr. The cooled reaction mixture was then filtered and concentrated in vacuo. The residue was dissolved in $Et_2O$ and treated with excess ethereal HCl. The mixture was then concentrated to a solid. The solid was treated with EtOAc and collected by filtration. The product was then partitioned betveen EtOAc and 2N $Na_2CO_3$. The organics were dried over $MgSO_4$. filtered, and concentrated in vacuo to afford methyl 4-[4-[4-(hydroxydiphenylmethyl)-1-piperidinyl]-1-oxobutyl]-α,α-dimethylphenylacetate.

Example 7

Preparation of Methyl 4-[4-[4-(Hydroxydiphenylmethyl)-1-piperidinyl]-1-hydroxybutyl]-α,α-dimethylphenylacetate A solution of 13.5 g of methyl 4-[4-[4-(hydroxydiphenylmethyl)-1-piperidinyl]-1-oxobutyl]-α,α-dimethylphenylacetate in 250 mL of $CH_3OH$ is cooled in an ice $CH_3OH$ bath, and 1.8 g of $NaBH_4$ was added in portions. After 1 hr, the mixture was concentrated to a solid. The residue was partitioned between EtOAc and saturated aqueous $NaHCO_3$. The aqueous portion was extracted with EtOAc. The combined organics were washed with saturated aqueous NaCI, dried over $MgSO_4$, filtered, and concentrated in vacuo to afford methyl 4-[4-[4-(hydroxydiphenyimethyl)-1-piperidinyl]-1-hydroxybutyl]-α,α-dimethylphenylacetate as a foam.

Example 8

Preparation of 4-[4-[4-Hydroxydiphenylmethyl)-1-piperidinyl]-1-hydroxybutyl]-α,α-dimethylphenylacetic Acid To a solution of 9.5 g of methyl-4-[4-[4-(hydroxydiphenylmethyl)-1-piperidinyl]-1-hydroxybutyl]-α,α-dimethylphenylacetate in 300 mL of $CH_3OH$ and 150 mL of $H_2O$, was added 10 g of NaOH. The mixture was refluxed for lhr, then cooled. The $CH_3OH$ was removed in vacuo. The concentrate was diluted with $H_2O$ and $CHCl_3$, and the pH is adjusted to approximately 5.5 to 6.0. The phases were separated, and the aqueous phase was extracted with $CHCl_3$. The combined organics were dried over $MgSO_4$, filtered, and stripped to afford crude product.

The crude product was dissolved in $CH_2Cl_2$ and chiromatographed on Davisil Grade 633 $SiO_2$ eluting with a gradient of $CHCl_3$, to 10% $CH_3OH$ in $CHCl_3$, to 25% $CH_3OH$ in $CHCl_3$. The product containing fractions were concentrated to afford 4-[4-[4-hydroxydiphenylmethyl)-1-piperidinyl]-1-hydroxybutyl]-α,α-dimethylphenylacetic acid.

Example 9

Preparation of Methyl 4-[4-[4-(Bis(4-methylphenyl) hydroxymethyl)-1-piperidinyl]-1-oxobutyl]-α,α-dimethylphenylacetate To a solution of 6.4 g (0.017 mol) of methyl 4-(4-chloro-1-oxobutyl)-α,α-dimethylphenylacetate in 500 mL of toluene in a one liter round bottom flask equipped with a mechanical stirrer was added 5.1 g (0.017 mol) of 4-(α,α-bis(4-methylphenyl)-piperidinemethanol, followed by 11.8 g (0.086 mol) of solid potassium carbonate. The solution was heated to reflux for 24 hr. After cooling, the mixture was filtered, and the toluene was removed in vacuo. The residue was partitioned between ethyl acetate and 2 N sodium carbonate solution. The aqueous layer was extracted twice with ethyl acetate, the combined organic layers were dried with sodium sulfate, and the ethyl acetate was removed in vacuo to provide methyl 4-[4-[4-(bis(4-methylphenyl) hydroxymethyl)-1-piperidinyl]-1-oxobutyl]-α,α-dimethylphenylacetate.

Example 10

Preparation of Methyl 4-[4-[4-(Bis(4-Methylphenyl) hydroxymethyl)-1-piperidinyl]-1-hydroxybutyl]-α,α-dimethylphenylacetate To a -10° C. solution of 6.8 g (0.013 mol) of methyl 4-[4-[4-(bis(4-methylphenyl)hydroxymethyl)-1-piperidinyl]-1-oxobutyl]-α,α-dimethylphenylacetate in 150 mL of methanol in a 500 mL round bottom flask equipped with a mechanical stirrer was slowly added 0.86 g (0.023 mol) of sodium borohydride, and the reaction was stirred for 2 hr. The methanol was removed in vacuo, and the residue was partitioned between ethyl acetate and aqueous sodium bicarbonate solution. The aqueous layer was extracted with ethyl acetate, the combined organic layers were dried with sodium sulfate, and the ethyl acetate was removed in vacuo to provide crude product. The resultant material was purified by column chromatography (Davisil grade 633 silica gel, packed in metlhylene chloride, material applied in chloroform, and eluted with a gradient of 2% methanol to methylene chloride to 5% methanol to methylene chloride) to afford methyl 4-[4-[4-(bis(4-methylphenyl) hydroxymethyl) 1-piperidinyl]-1-hydroxybutyl]-α,α-dimethylphenylacetate.

Example 11

Preparation of 4-[4-[4-(Bis(4-metthylphenyl) hydroxymethyl)-1-piperidinyl]-1-hydroxybutyl]-α, α-dimethylphenylacetic Acid To 350 mL of methanol in a 1 L round bottom flask equipped with a mechanical stirrer was added 5.3 g (9.8 mmol) of methyl 4-[4-[4-(bis(4-methylphenyl) hydroxymethl)-1-piperidinyl]-1-hydroxybutyl]-α,α-dimethylphenylacetate, 5.1 g (0. 13 mol) of solid sodium hydroxide, and 100 mL of water. The mixture was heated to reflux for 3 hr. After cooling, the methanol was removed in vacuo, and 6 N hydrochloric acid was added dropwise until the solution was no longer basic (pH=7). The solution was extracted three times with ethyl acetate. The organic layers were combined, and precipitation is induced. The solid was washed with ether to provide 4-[4-[4-(bis(4-methylphenyl) hydroxymethyl)-1-piperdindl]-1-hydroxybutyl]-α,α-dimethylphlienlacetic acid, as the dihydrate.

Example 12

Preparation of 4-(1-Hydroxy-4-chlorobutyl)-α,α-dimethylphenylacetic Acid

To a solution of 50 mg of 4-(4-chloro-1-oxobutyl)-α,α-dimethylphenylacetic acid in 3 mL of methanol was added 50 mg of NaBH$_4$. The mixture was stirred for 30 minutes, acidified with 2N HCl, and the methanol was removed in vacuo. The concentrate was extracted with EtOAc. The orcanlics were dried over Na$_2$SO$_4$, filtered, and concentrated to afford 4-(1-hydroxy-4-chlorobutyl)-α,α-dimethylphenylacetic acid.

Example 13

Preparation of 4-[4-[4-(Hydroxydiphenylmethyl)-1-piperidinyl]-1-oxobutyl]-α,α-dimethilplenylacetic Acid A mixture of 800 mg of 4-(4-chloro-1-oxobutyl)-α,α-dimethylphenylacetic acid, 800 mg of 4-(α,α-diphenyl) piperidinemethaiiol, and 2.4 g of K$_2$CO$_3$ in 25 mL of toluene was stirred for 48 hours at room temperature. The mixture was concentrated in vacuo. The residue was treated with EtOAc. filtered, and concentrated to afford 4-[4-[4-(hydroxydiphenylmethyl)-1-pipridinyl]-1-oxobutyl]-α,α-dimethylphenylacetic acid.

Example 14

Preparation of 4-[4-[4-Hydroxydiphenylmethyl)-1-piperidinyl]-1-hydroxybutyl]-α,α-dimethylplenylacetic Acid A mixture of 4-[4-[4-(hydroxydiplienylmethyl)-1-piperidinyl]-1-oxobutyl]-α,α-dimethylphenylacetic acid, and 300 mg of NaBH$_4$ in 25 mL of CH$_3$OH was stirred overnight at room temperature. The mixture was then concentrated in vacuo. The residue was partitioned between EtOAc and H$_2$O. The aqueous portion was treated with concentrated HCl until pH 6, then extracted w ith EtOAc. The organics were concentrated in vacuo. The residue was dissolved in EtOAc. filtered, and concentrated in vacuo to an oil. The oil was dissolved in CH$_3$OH and concentrated to a solid. The solid was slurried with EtOAc, filtered, and rinsed with EtOAc to afford 4-[4-[4-hydrox)diphenylmethyl)-1-piperidinyl]-1-hydroxybutyl]-α,α-dimethylphenylacetic acid.

Although the invention has been described in detail for the purpose of illustration, it is understood that such detail is solely for that purpose, and variations can be made therein by those skilled in the art without departing from the spirit and scope of the invention which is defined by the following claims.

What is claimed:
1. A process of preparing a piperidine derivative compound of the formula:

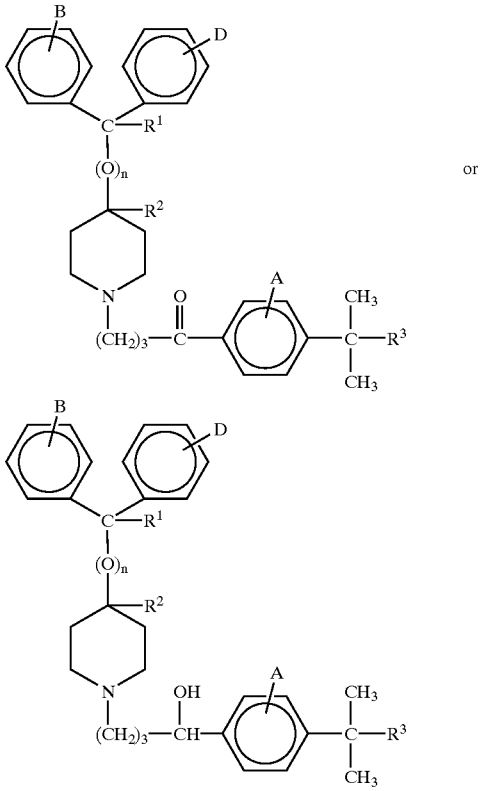

wherein
  n is 0 or 1;
  $R^1$ is hydrogen or hydroxy;
  $R^2$ is hydrogen;
  or, when n is 0, $R^1$ and $R^2$ taken together form a second bond between
the carbon atoms bearing $R^1$ and $R^2$, provided that when n is 1, $R^1$ and $R^2$ are each hydrogen;
  $R^3$ is —COOH or —COOR$^4$;
  $R^4$ is an alkyl or aryl moiety;
  A, B, and D are the substituents of their rings, each of which may be different or the same, and are selected from the group consisting of hydrogen, halogens, alkyl, hydroxy, alkoxy, and other substituents;
said process comprising:
  providing a reioisomer of the following formula:

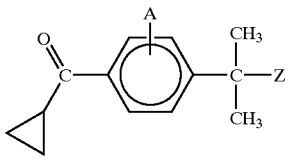

wherein
Z is

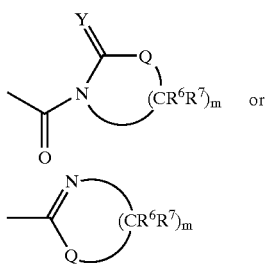

or

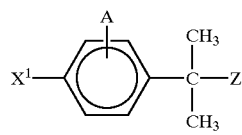

m is 1 or 3–6;
Q and Y are the same or different and are selected from the group consisting of O, S, and $NR^5$;
$R^6$ and $R^7$ are the same or different and are selected from the group consisting of hydrogen, an alkyl moiety, an aryl moiety, $OR^8$, $SR^8$, and $NR^8R^9$; and
$R^5$, $R^8$, and $R^9$ are the same or different and are selected from the group consisting of hydrogen, an alkyl moiety, and an aryl moiety, wherein said providing is carried out by a process selected from the proup consisting of:

1) acylatino, an α,α-disubstituted-methylbenzene derivative having the formula:

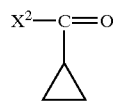

wherein
$X^1$ is a halogen, trialkyl or triaryl tin, trialkyl or triaryl borate, trialkyl silicon, alkylhalo silicon, a substituted sulfonic ester, or substituents useful in organometallic coupling reactions
with a compound having the formula:

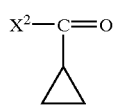

wherein
$X^2$ is a halogen, an alkali metal oxide; a moiety having the formula $—OR^{10}$; a moiety having the formula $—SR^{10}$; or an amine; and
$R^{10}$ is selected from the group consisting of hydrogen, an alkyl moiety, and an aryl moiety
under non-Friedel-Crafts acylation conditions effective to produce the repioisomer, 2) reacting a 4-(α,α-disubstituted)-toluic acid derivative having the formula:

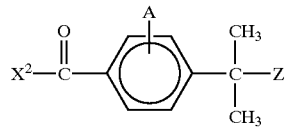

wherein
$X^2$ is hydrogen; a halogen; an alkali metal oxide; a moiety having the formula $—OR^{10}$; a moiety having the formula $—SR^{10}$; or an amine; and $R^{10}$ is selected from the group consisting of hydrogen, an alkyl moiety, and an aryl moiety
with a compound having the formula:

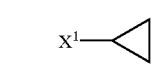

wherein
$X^1$ is a halogen, trialkyl or triaryl tin, trialkyl or triaryl borate, trialkyl silicon, alkylhalo silicon, a substituted sulfonic ester, or substituents useful in organometallic coupling reactions
under non-Friedel-Crafts reaction conditions effective to produce the regioisomer, 3) acylating an α,α-diunsubstitued-methylbenzene derivative having the formula:

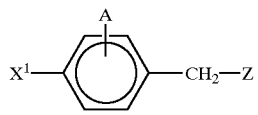

wherein
$X^1$ is a halogen, trialkyl or triaryl tin, trialkyl or triaryl borate, trialkyl silicon, alkylhalo silicon, a substituted sulfonic ester, or substituents useful in organometallic coupling reactions
with a compound having the formula:

$X^2—C=O$ wherein
$X^2$ is a halopen; an alkali metal oxide; a moiety having the formula $—OR^{10}$; a moiety having the formula $—SR^{10}$; or an amine; and
$R^{10}$ is selected from the group consistinw of hydrogen, an alkyl moiety, and an aryl moiety
under non-Friedel-Crafis reaction conditions effective to produce an α,α-diunsubstitued regioisomer precursor of the formula

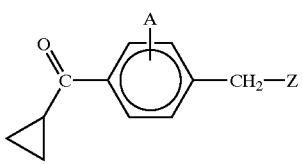

and methylating the α,α-diunsubstituted repioisomer precursor under conditions effective to produce the regioisomer, and 4) reacting a 4-(α,α-diunsubstituted-)toluic acid derivative having the formula:

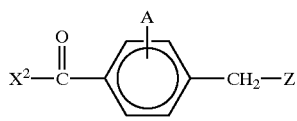

wherein
- $X^2$ is hydrogen; a halogen; an alkali metal oxide; a moiety having the formula —$OR^{10}$; a moiety having the formula —$SR^{10}$; or an amine; and
- $R^{10}$ is selected from the group consisting of hydrogen, an alkyl moiety, and an aryl moiety with a compound having the formula:

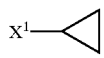

wherein
- $X^1$ is a halogen, trialkyl or triaryl tin, trialkyl or triaryl borate, trialkyl silicon, alkylhalo silicon, a substituted sulfonic ester, or substituents useful in organometallic coupling reactions under non-Friedel-Crafts reaction conditions effective to produce an α,α-diunsubstitued regioisomer precursor of the formula

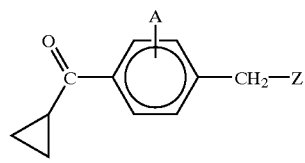

and methylating the a α,α-diunsubstituted repioisomer precursor under conditions effective to produce the regioisomer;

and converting the regioisomer to the piperidine derivative compound with a piperidine compound.

2. A process according to claim 1, wherein said providing the regioisomer comprises:

acylating an α,α-disubstituted-methylbenzene derivative having the formula:

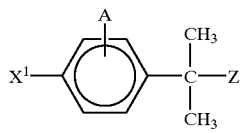

wherein
- $X^1$ is a halogen, trialkyl or triaryl tin, trialkyl or triaryl borate, trialkyl silicon, alkylhalo silicon, a substituted sulfonic ester, or substituents useful in organometallic coupling reactions with a compound having the formula:

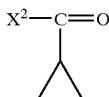

wherein
- $X^2$ is a halogen; an alkali metal oxide; a moiety having the formula —$OR^{10}$; a moiety having the formula —$SR^{10}$; or an amine; and
- $R^{10}$ is selected from the group consisting of hydrogen, an alkyl moiety, and an aryl moiety under non-Friedel-Crafts acylation conditions effective to produce the regioisomer.

3. A process according to claim 2 further comprising:

reacting an α,α-diunsubstituted-methylbenzene derivative having the formula:

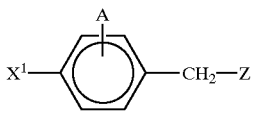

with a methylating agent under conditions effective to produce the α-αdisubstituted-methylbenzene derivative.

4. A process according to claim 3, wherein Z has the formula:

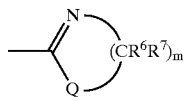

and further comprising reacting an α,α-diunsubstituted benzylic acid derivative having the formula:

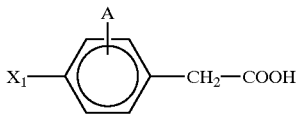

with an aminoalkyl derivative having the formula:

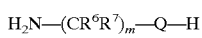

under conditions effective to produce the a, α,α-diunsubstituted-methylbenzene derivative.

5. A process according to claim 2, wherein Z has the formula:

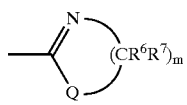

and further comprising:

reacting an α,α-disubstituted benzylic acid derivative having the formula:

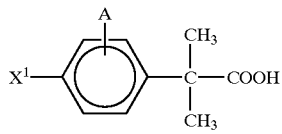

with an aminoalkyl derivative having the formula:

under conditions effective to produce the α,α-disubstituted-methylbenzene derivative.

6. A process according to claim 1, wherein said providing the regioisomer comprises:

reacting a 4-(α,α-disubstituted)-toluic acid derivative having the formula:

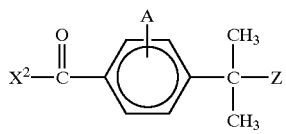

wherein $X^2$ is hydrogen; a halogen; an alkali metal oxide; a moiety having the formula —$OR^{10}$; a moiety having the formula —$SR^{10}$; or an amine; and $R^{10}$ is selected from the group consisting of hydrogen, an alkyl moiety, and an aryl moiety with a compound having the formula:

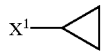

wherein $X^1$ is a halogen, trialkyl or triaryl tin, trialkyl or triaryl borate, trialkyl silicon, alkylhalo silicon, a substituted sulfonic ester, or substituents useful in organometallic coupling reactions under non-Friedel-Crafts reaction conditions effective to produce the regioisomer.

7. A process according to claim 6, further comprising:

reacting a 4-(α,α-diunsubstituted)-toluic acid derivative having the formula:

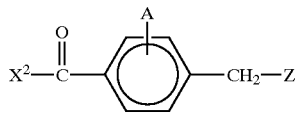

with a methylating agent under conditions effective to produce the 4-(α,α-disubstituted)-toluic acid derivative.

8. A process according to claim 7, wherein Z has the formula:

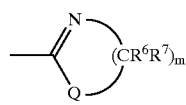

and further comprising:

reacting a 4-(α-carboxy-α,α-diunsubstituted)-toluic acid derivative having the formula:

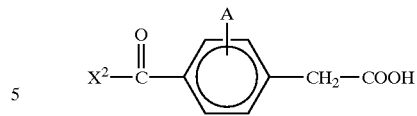

with an aminoalkyl derivative having the formula:

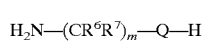

under conditions effective to produce the 4-α,α-diunsubstituted)-toluic acid derivative.

9. A process according to claim 6, wherein Z has the formula:

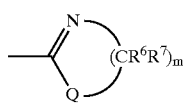

and further comprising:

reacting a 4-(α-carboxy-α,α-disubstituted)-toluic acid derivative having the formula:

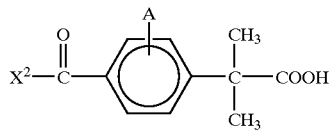

with an aminoalkyl derivative having the formula:

under conditions effective to produce the 4-(α,α-disubstituted)-toluic acid derivative.

10. A process according to claim 1, wherein said providing a regioisomer comprises:

acylating an α,α-diunsubstitued-methylbenzene derivative having the formula:

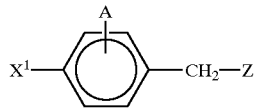

wherein $X^1$ is a halogen, trialkyl or triaryl tin, trialkyl or triaryl borate, trialkyl silicon, alkylhalo silicon, a substituted sulfonic ester, or substituents useful in organometallic coupling reactions with a compound having the formula:

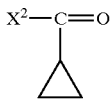

wherein $X^2$ is a halogen; an alkali metal oxide; a moiety having the formula —$OR^{10}$; a moiety having the formula —$SR^{10}$; or an amine; and $R^{10}$ is selected from the group consisting of hydrogen, an alkyl moiety, and an aryl moiety under non-Friedel-Crafts reaction conditions effective to produce an α,α-diunsubstitued regioisomer precursor of the formula

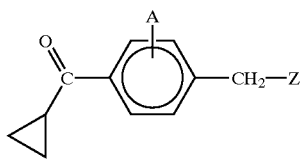

and
methylating, the α,α-diunsubstituted regioisomer precursor under conditions effective to produce the regioisomer.

11. A process according to claim 1, wherein said providing a regioisomer comprises:
reacting a 4-(α,α-diunsubstitued)-toluic acid derivative having the formula:

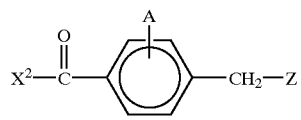

wherein
$X^2$ is hydrogen; a halogen; an alkali metal oxide; a moiety having the formula —$OR^{10}$; a moiety having the formula —$SR^{10}$; or an amine; and
$R^{10}$ is selected from the group consisting of hydrogen, an alkyl moiety, and an aryl moiety
with a compound having the formula:

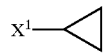

wherein
$X^1$ is a halogen, trialkyl or triaryl tin, trialkyl or triaryl borate, trialkyl silicon, alkylhalo silicon, a substituted sulfonic ester, or substituents useful in organometallic coupling reactions
under non-Friedel-Crafis reaction conditions effective to produce an α,α-diunsubstitued regioisomer precursor of the formula

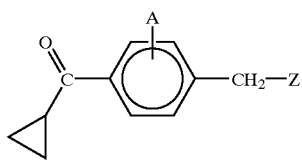

and
methylating the α,α-diunsubstituted regioisomer precursor under conditions effective to produce the regioisomer.

12. A process according to claim 1, further comprising:
reducing the piperidine derivative compound under conditions effective to form a hydroxylated piperidine derivative compound of the formula:

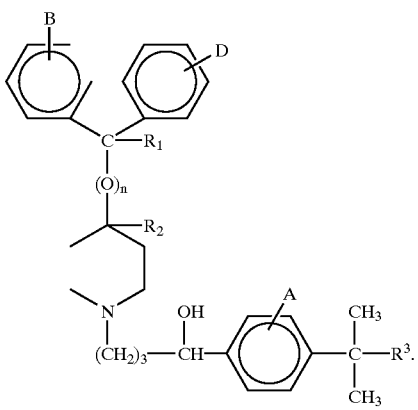

13. A process according to claim 12, wherein the hyrdroxylated piperidine derivative compound has the formula:

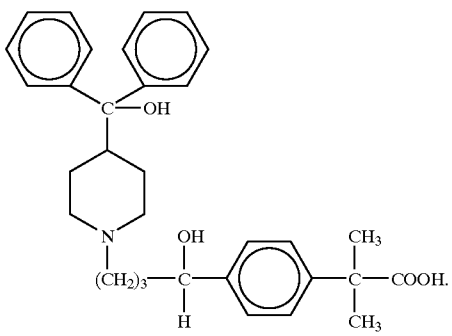

14. A process according to claim 12, wherein the hydroxylated piperidine derivative compound has the formula:

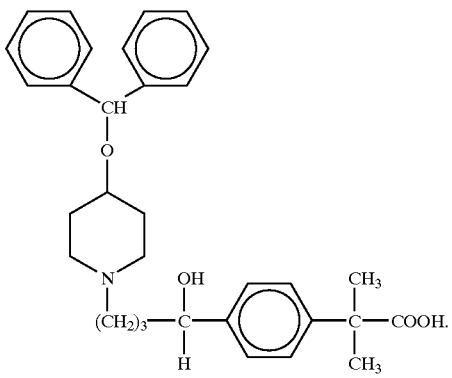

15. A process according to claim 1, wherein the piperidine derivative compound has the formula:

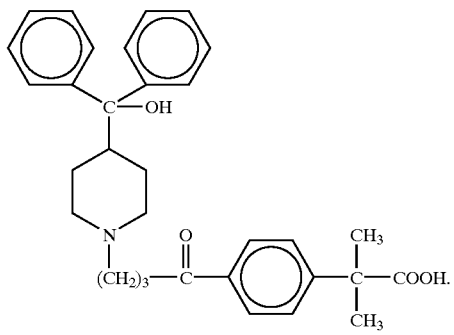

16. A process according to claim 1, wherein the piperidine derivative compound has the formula:

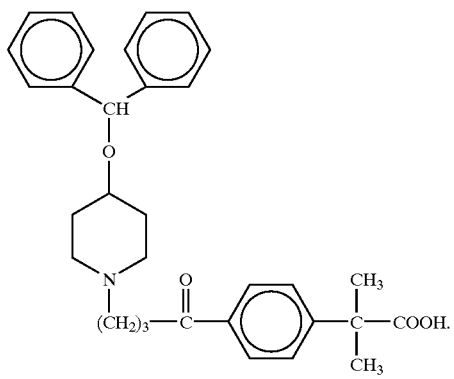

17. A process according to claim 1, wherein said converting comprises:

halogenating the regioisomer of the formula:

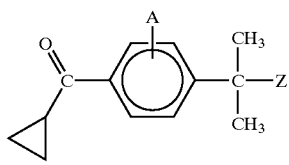

under conditions effective to form a first intermediate compound of the formula:

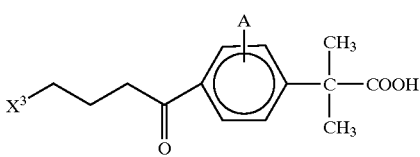

wherein $X^3$ is a halogen or a hydroxy, alkoxy, or aryloxy moiety.

18. A process according to claim 17, wherein said halogenating comprises sequentially:

decyclizing the regioisomer to produce an oxobutyl derivative having the formula:

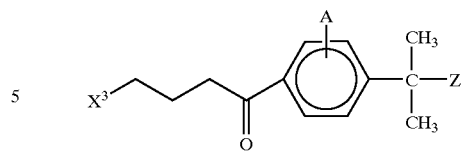

and then converting the oxobutyl derivative to the first intermediate compound.

19. A process according to claim 17, wherein said converting further comprises:

reacting the first intermediate compound with a piperidine compound of the formula:

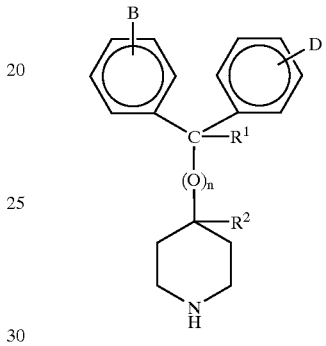

under conditions effective to form the piperidine derivative compound of the formula:

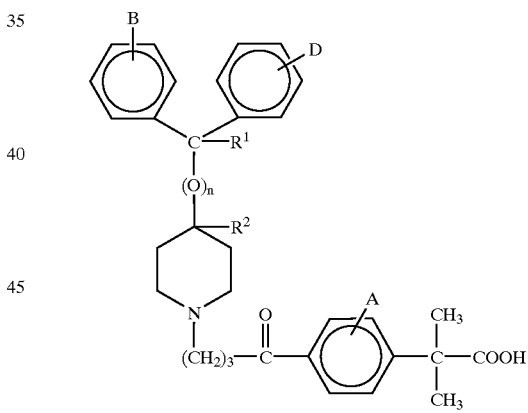

20. A process according to claim 17, wherein said converting further comprises:

esterifying the first intermediate compound to the ester thereof, having the formula:

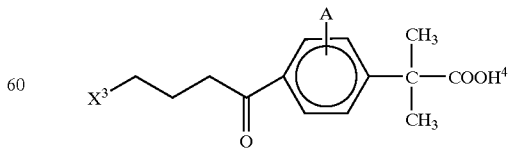

and reacting the ester with a piperidine compound of the formula:

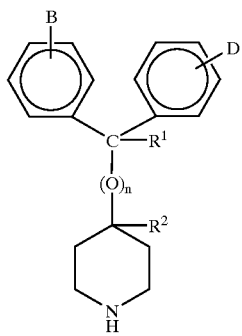

under conditions effective to form the piperidine derivative compound of the formula:

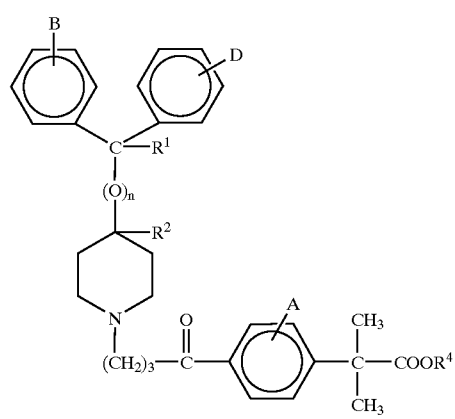

21. A process according to claim 20, further comprising:

hydrolyzing the piperidine derivative compound of the formula:

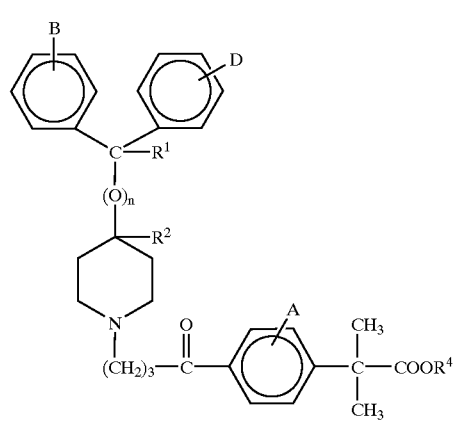

to a piperldine derivative compound of the formula:

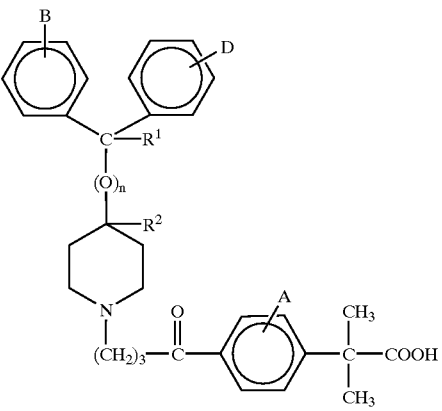

22. A process according to claim 17, wherein n is 1 and wherein said converting further comprises:

reacting the first intermediate compound with 4-hydroxypiperidine under conditions effective to produce an N-substituted hydroxypiperidine having the formula:

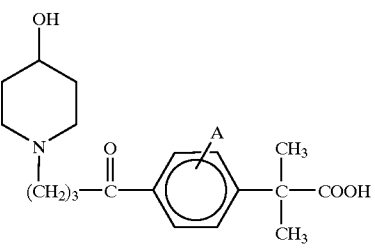

and reacting the N-substituted hydroxypiperidine with a diarylhalomethane having the formula:

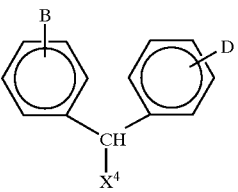

wherein $X^4$ is a halogen under conditions effective to form the piperidine compound derivative of the formula:

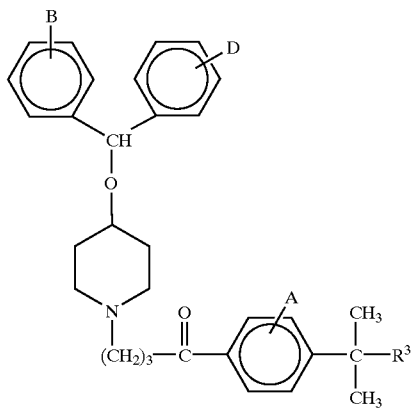

23. A process according to claim 1, wherein said converting comprises:

decyclizing the regioisomer of the formula:

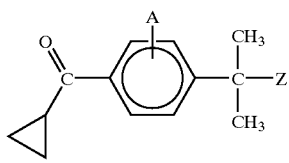

under conditions effective to form an oxobutyl derivative of the formula:

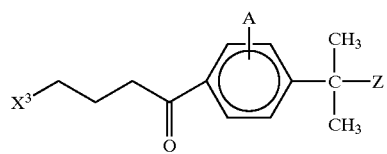

wherein $X^3$ is a halogen or a alkoxy or aryloxy moiety.

24. A process according to claim 23, wherein said converting further comprises:

reacting the oxobutyl derivative with a piperidine compound of the formula:

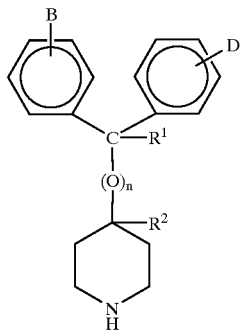

under conditions effective to form the piperidine derivative precursor of the formula:

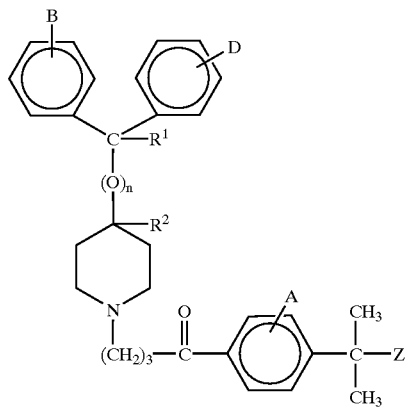

25. A process according to claim 24, further comprising converting the piperidine derivative precursor to the piperidine derivative compound of the formula:

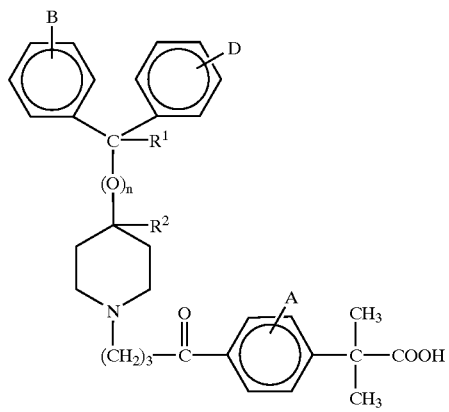

26. A process according to claim 24, further comprising reducing the piperidine derivative precursor under conditions effective to form a hydroxylated piperidine derivative precursor of the formula:

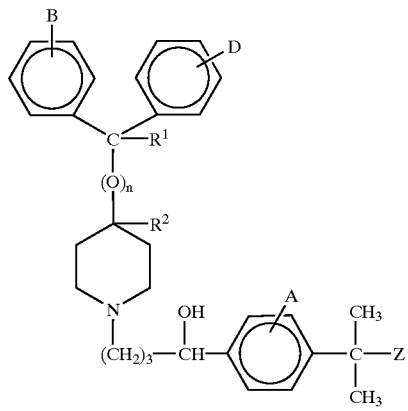

27. A process according to claim 26, further comprising converting the hydroxylated piperidine derivative precursor to a hydroxylated piperidine derivative compound of the formula:

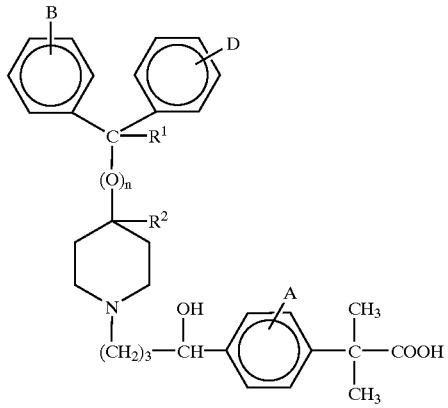

28. A process according to claim 23, wherein n is 1 and wherein said converting further comprises:

reacting the oxobutyl derivative with 4-hydroxypiperidine under conditions effective to produce an N-substituted-hydroxypiperidine having the formula:

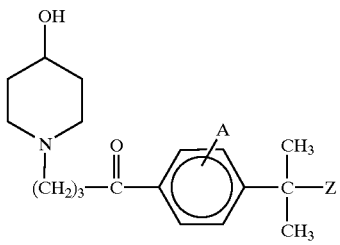

and reacting the N-substituted hydroxypiperidine with a diaryihalomethalne having the formula:

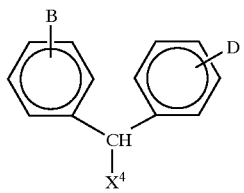

wherein $X^4$ is a halogen under conditions effective to form the piperidine derivative precursor of the formula:

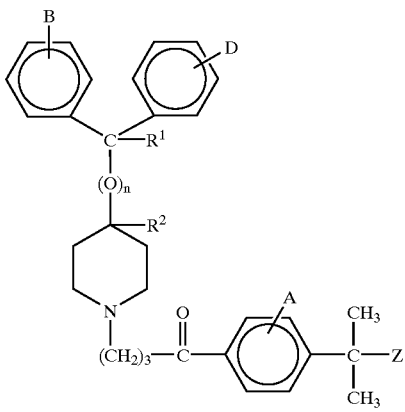

29. A process according to claim 28, further comprising converting the piperidine derivative precursor to the piperidine derivative compound of the formula:

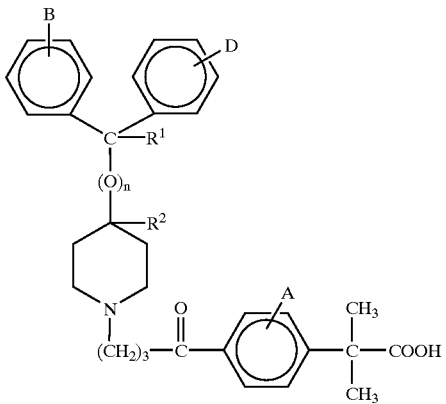

30. A process according to claim 28, further comprising reducing the piperidine derivative precursor under conditions effective to form a hydroxylated piperidine derivative precursor of the formula:

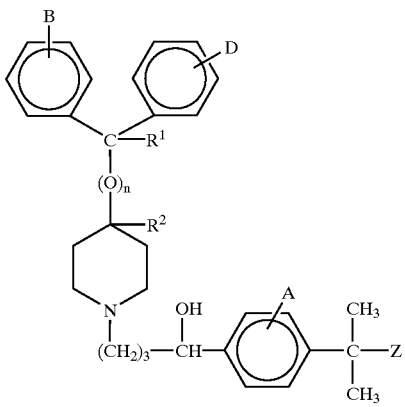

31. A process according to claim 30, further comprising:

converting the hydroxylated piperidine derivative precursor to a hydroxylated piperidine derivative compoundof the formula:

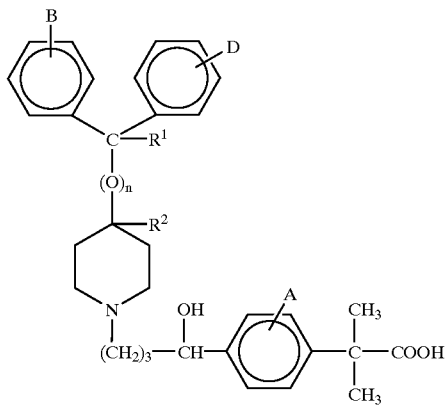

32. A process of preparing a regioisomer of the formula:

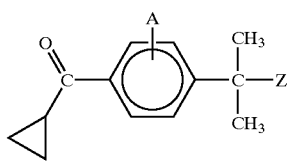

wherein
Z is

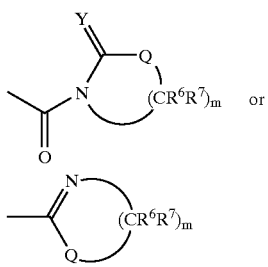

m is 1 or 3–6;
Q and Y are the same or different and are selected from the group consisting of O, S, and $NR^5$;
$R^6$ and $R^7$ are the same or different and are selected from the group consisting of hydrogen, an alkyl moiety, an aryl moiety, $OR^8$, $SR^8$, and $NR^8R^9$;
$R^5$, $R^8$, and $R^9$ are the same or different and are selected from the group consisting of hydrogen, an alkyl moiety, and an aryl moiety; and
A is the substituents of its ring, each of which may be different or the same and are selected from the group consisting of hydrogen, halogens, alkyl, hydroxy, alkoxy, and other substituents,
said process comprising
acylating an α,α-disubstituted-methylbenzene derivative having the formula:

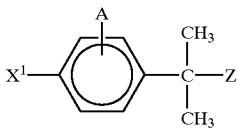

wherein $X^1$ is a halogen, trialkyl or triaryl tin, trialkyl or triaryl borate, trialkyl silicon, alkylhalo silicon, a substituted sulfonic ester, or substituents useful in organometallic coupling reactions with a compound having the formula:

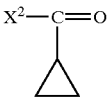

wherein $X^2$ is a halogen; an alkali metal oxide; a moiety having the formula $-OR^{10}$; a moiety having the formula $-SR^{10}$; or an amine; and $R^{10}$ is selected from the group consisting of hydrogen, an alkyl moiety, and an aryl moiety under non-Friedel-Crafts reaction conditions effective to produce the regioisomer.

33. A process to claim 32 further comprising:

reacting an α,α-diunsubstitued-methylbenzene drivative having the formula:

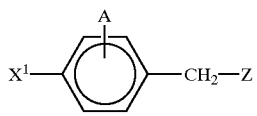

with a methylating agent under conditions effective to produce the α,α-diunsubstitued-methylbenzene drivative.

34. A process according to claim 33, wherein Z has the formula:

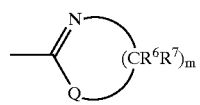

and further comprising reacting an α,α-diunsubstituted benzylic acid derivative having the formula:

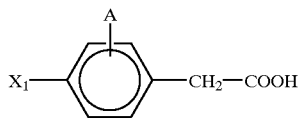

with an aminoalkyl derivative having the formula:

under conditions effective to produce the α,α-diunsubstituted-methylbenzene derivative.

35. A process according to claim 32, wherein Z has the formula:

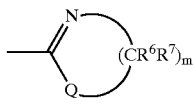

and further comprising:

reacting an α,α-disubstituted benzylic acid derivative having the formula:

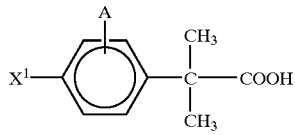

with an aminoalkyl derivative having the formula:

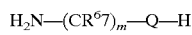

under conditions effective to produce the α,α-disubstituted-methylbenzene derivative.

36. A process of preparing a regioisomer of the formula:

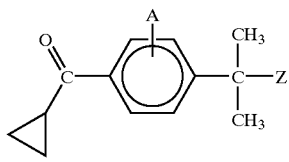

wherein

Z is

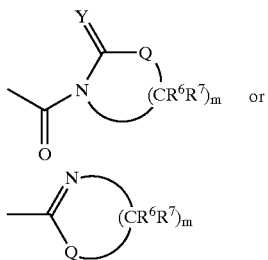

m is 1 or 3–6;

Q and Y are the same or different and are selected from the group consisting of O, S, and $NR^5$;

$R^6$ and $R^7$ are the same or different and are selected from the group consisting of hydrogen, an alkyl moiety, an aryl moiety, $OR^8$, $SR^8$, and $NR^8R^9$;

$R^5$, $R^8$, and $R^9$ are the same or different and are selected from the group consisting of hydrogen, an alkyl moiety, and an aryl moiety; and A is the substituents of its ring, each of which may be different or the same and are selected from the group consisting of hydrogen, halogens, alkyl, hydroxy, alkoxy, and other substituents, said process comprising:

reacting a 4-(α,α-disubstituted)-toluic acid derivative having the formula:

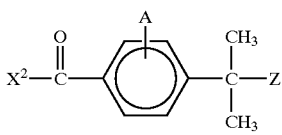

wherein $X^2$ is hydrogen; a halogen; an alkali metal oxide; a moiety having the formula $—OR^{10}$; a moiety having the formula $—SR^{10}$; or an amine; and $R^{10}$ is selected from the group consisting of hydrogen, an alkyl moiety, and an aryl moiety with a compound having the formula:

wherein $X^1$ is a halogen, trialkyl or triaryl tin, trialkyl or triaryl borate, trialkyl silicon, alkylhalo silicon, a substituted sulfonic ester, or substituents useful in organometallic coupling reactions under non-Friedel-Crafts reaction conditions effective to produce the regioisomer.

37. A process according to claim 36 further comprising:

reacting a 4-(α,α-diunsubstituted)-toluic acid derivative having the formula:

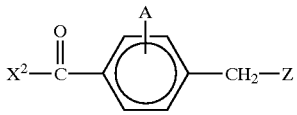

with a methylating agent under conditions effective to produce the 4-(α,α-disubstituted)-toluic acid derivative.

38. A process according to claim 37, wherein Z has the formula:

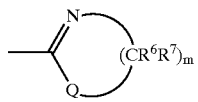

and further comprising:

reacting a 4-(α,-carboxy-α,α-diunsubstituted)-toluic acid derivative having the formula:

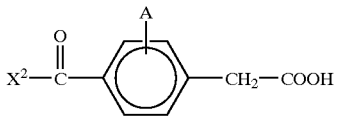

with an aminoalkyl derivative having the formula:

under conditions effective to produce the 4-(α,α-diunsubstituted)-toluic acid derivative.

39. A process according to claim 38, wherein Z has the formula:

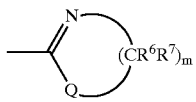

said process further comprising:

reacting an 4-(α-carboxy-(α,α-disubstituted)-toluic acid derivative having the formula:

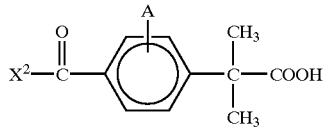

with an aminoalkyl derivative having the formula:

under conditions effective to produce the 4-(α,α-disubstituted)-toluic acid derivative.

40. A process of preparing a regioisomer of the formula:

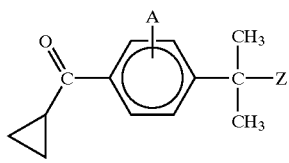

wherein

Z is

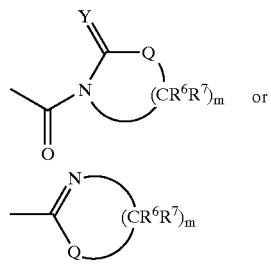

m is 1 or 3–6;

Q and Y are the same or different and are selected from the group consisting of O, S, and $NR^5$;

$R^6$ and $R^7$ are the same or different and are selected from the group consisting of hydrogen, an alkyl moiety, an aryl moiety, $OR^8$, $SR^8$, and $NR^8R^9$;

$R^5$, $R^8$, and $R^9$ are the same or different and are selected from the group consisting of hydrogen, an alkyl moiety, and an aryl moiety; and A is the substituents of its ring, each of which may be different or the same and are selected from the group consisting of hydrogen, halogens, alkyl, hydroxy, alkoxy, and other substituents, said process comprising:

providing an α,α-diunsubstituted regioisomer precursor prepared under non-Friedel-Crafts reaction conditions and having the formula:

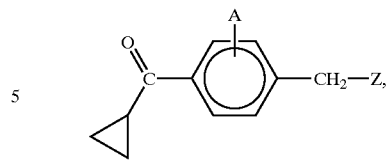

wherein said providing is selected from the group consisting of:

1) acylating an α,α-diunsubstituted-methylbenzene derivative having the formula:

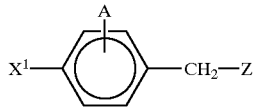

wherein $X^1$ is a halogen, trialkyl or triaryl tin, trialkyl or triaryl borate, trialkyl silicon, alkylhalo silicon, a substituted sulfonic ester, or substituents useful in organometallic coupling reactions with a compound having the formula:

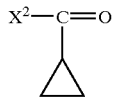

wherein $X^2$ is a halogen; an alkali metal oxide; a moiety having the formula —$OR^{10}$; a moiety having the formula —$SR^{10}$; or an amine; and $R^{10}$ is selected from the group consisting of hydrogen, an alkyl moiety, and an aryl moiety under non-Friedel-Crafts acylation conditions effective to produce the α,α-diunsubstituted regioisomer precursor, and 2) acylating a 4-(α,α-diunsubstituted)-toluic acid derivative having the formula:

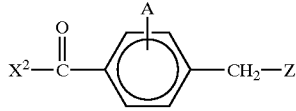

wherein $X^2$ is a halogen; an alkali metal oxide; a moiety having the formula —$OR^{10}$; a moiety having the formula —$SR^{10}$; or an amine; and $R^{10}$ is selected from the group consisting of hydrogen, an alkyl moiety, and an aryl moiety with a compound having the formula:

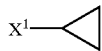

wherein $X^1$ is a halogen, trialkyl or triaryl tin, trialkyl or triaryl borate, trialkyl silicon, alkylhalo silicon, a substituted sulfonic ester, or substituents useful in organometallic coupling reactions under non-Friedel-Crafts reaction conditions effective to produce the α,α-diunsubstituted regioisomer precursor, and methylating the α,α-diunsubstituted regioisomer precursor under conditions effective to produce the regioisomer.

41. A process according to claim 40, wherein said providing the α,α-diunsubstituted regioisomer precursor comprises:

acylating an α,α-diunsubstituted-methylbenzene derivative having the formula:

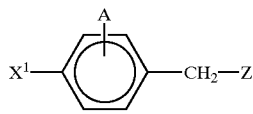

wherein $X^1$ is a halogen, trialkyl or triaryl tin, trialkyl or triaryl borate, trialkyl silicon, alkyihalo silicon, a substituted sulfonic ester, or substituents useful in organometallic coupling reactions with a compound having the formula:

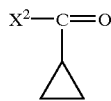

wherein $X^2$ is a halogen; an alkali metal oxide; a moiety having the formula $-OR^{10}$; a moiety having the formula $-SR^{10}$; or an amine; and $R^{10}$ is selected from the group consisting of hydrogen, an alkyl moiety, and an aryl moiety under non-Friedel-Crafts reaction conditions effective to produce the α,α-diunsubstituted regioisomer precursor.

42. A process according to claim 40, wherein said providing the α,α-diunsubstituted regioisomer precursor comprises:

acylating a 4-(α,α-diunsubstituted)-toluic acid derivative having the formula:

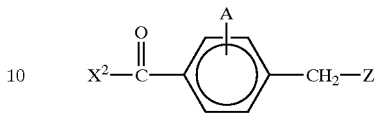

wherein $X^2$ is a halogen; an alkali metal oxide; a moiety having the formula $-OR^{10}$; a moiety having the formula $-SR^{10}$; or an amine; and $R^{10}$ is selected from the group consisting of hydrogen, an alkyl moiety, and an aryl moiety with a compound having the formula:

wherein $X^1$ is a halogen, trialkyl or triaryl tin, trialkyl or triaryl borate, trialkyl silicon, alkylhalo silicon, a substituted sulfonic ester, or substituents useful in organometallic coupling reactions under non-Friedel-Crafts reaction conditions effective to produce the α,α-diunsubstituted regioisomer precursor.

* * * * *